US009208288B2

(12) United States Patent
Putrino

(10) Patent No.: US 9,208,288 B2
(45) Date of Patent: Dec. 8, 2015

(54) SYSTEM AND METHOD FOR REMOTE PATIENT MONITORING AND ASSESSMENT TO FACILITATE PATIENT TREATMENT

(76) Inventor: Roy C Putrino, Wychoff, NJ (US)

( * ) Notice: Subject to any disclaimer, the term of this patent is extended or adjusted under 35 U.S.C. 154(b) by 523 days.

(21) Appl. No.: 12/861,403

(22) Filed: Aug. 23, 2010

(65) Prior Publication Data

US 2012/0044070 A1 Feb. 23, 2012

(51) Int. Cl.
*G08B 1/08* (2006.01)
*G06F 19/00* (2011.01)

(52) U.S. Cl.
CPC ........ *G06F 19/3487* (2013.01); *G06F 19/3468* (2013.01); *G06F 19/3418* (2013.01)

(58) Field of Classification Search
CPC ... G06F 19/3418; A61B 5/0002; G06Q 50/22
USPC ....................................................... 340/539.1
See application file for complete search history.

(56) References Cited

U.S. PATENT DOCUMENTS

| | | | |
|---|---|---|---|
| 5,289,540 A * | 2/1994 | Jones | 713/165 |
| 6,637,649 B2 * | 10/2003 | Walsh | 235/380 |
| 6,830,549 B2 | 12/2004 | Bui et al. | |
| 7,156,808 B2 | 1/2007 | Quy | |
| 7,249,036 B2 * | 7/2007 | Bayne | 705/2 |
| 2003/0140928 A1 * | 7/2003 | Bui et al. | 128/898 |
| 2004/0122707 A1 * | 6/2004 | Sabol et al. | 705/2 |
| 2004/0235446 A1 | 11/2004 | Flaherty et al. | |
| 2007/0214014 A1 * | 9/2007 | Suwalski et al. | 705/3 |
| 2008/0071217 A1 | 3/2008 | Moubayed et al. | |
| 2008/0154177 A1 * | 6/2008 | Moubayed et al. | 604/19 |
| 2008/0262872 A1 | 10/2008 | Perry et al. | |
| 2009/0171166 A1 * | 7/2009 | Amundson et al. | 600/301 |
| 2009/0171312 A1 | 7/2009 | Moubayed et al. | |
| 2009/0177769 A1 * | 7/2009 | Roberts | 709/224 |

OTHER PUBLICATIONS

"Infusion Software—Features and Benefits," printed on Jan. 5, 2011, available prior to Aug. 23, 2010, http://www.cprplus.com/infusion/featuressandbenefits.php (2 pages).
"Infusion Software—CPR+ Web Portal W/ Smartphone Integration," printed on Jan. 5, 2011, available prior to Aug. 23, 2010, http://www.cprplus.com/infusion/modules/mod-iv-webportal.php (1 page).

(Continued)

*Primary Examiner* — Kerri McNally
*Assistant Examiner* — Anthony D Afrifa-Kyei
(74) *Attorney, Agent, or Firm* — Michael P. Kochka, Esq.

(57) ABSTRACT

A system and method for remote patient monitoring and assessment to facilitate patient treatment are provided. The system includes at least one portable computing device (such as a smart cellular telephone) operated by a caregiver, which generates a plurality of user interface screens for allowing the caregiver to enter information relating to a patient's medical condition and treatment of the patient. The system compares a parameter of the information entered by the caregiver to a pre-defined threshold to determine whether the parameter is acceptable, and displays an alert screen on the portable computing device if the means for comparing the parameter determines that the parameter is unacceptable. A central server in communication with the portable computing device via a network receives the information entered by the caregiver, and electronically generates a report summarizing the patient's medical condition and treatment given to the patient by the caregiver.

17 Claims, 82 Drawing Sheets

(56) References Cited

OTHER PUBLICATIONS

"Infusion Software—CPR + Mobile," printed on Jan. 5, 2011, available prior to Aug. 23, 2010, http://www.cprplus.com/infusion/modules/mod-iv-mobile.php (1 page).

"CPR + Add on Modules," printed on Jan. 5, 2011, available prior to Aug. 23, 2010, http://www.cprplus.com/modules.php (1 page).

Humphrey, "4, 4, 7, B: The Path to Know," CPR+ Weekly Infusion—Issue #75, Apr. 28, 2009 (4 pages).

Van der Lek, "A Day in the Life of a Delivery Driver," CPR+ Weekly Infusion—Issue #127, Apr. 27, 2010 (4 pages).

* cited by examiner

FIG. 21

Skilled Nursing Visit Note

Are the lung sounds clear in all fields?  ◉ Yes  ◉ No

- ☑ Wheezing
- ☑ Rhonchi
- ☑ Rales
- ☑ Diminished Breath Sounds
- ☑ Cough
  - ☑ Productive
    - ☑ Thick
    - ☑ Thin
    - ☑ Green
    - ☑ Yellow
    - ☑ Clear

[Prev] [Next]

Concentration Change

Enter Change:

From: [Edit] /ml

To: [Edit] /ml

Reservoir Rinse Required?  ● Yes  ● No

How much Preservative free Normal Saline was used to perform Reservoir Rinse?

[Edit] mls of used

How many mls of the new medication was wasted during the rinse?

[Edit] mls

[Prev] [Next]

FIG. 62

Daily Dose Change

Drug: [Edit]
Current: [Edit] /day
Change to: [Edit] /day

Drug: [Edit]
Current: [Edit] /day
Change to: [Edit] /day

Drug: [Edit]
Current: [Edit] /day
Change to: [Edit] /day

[Prev] [Next]

Physician Info

Doctor Name: [Edit]

Address: [Edit]
[Edit]

City: [Edit]

State: [Edit]  Zip: [Edit]

Phone: [Edit]

Caregiver Info

Last Name: [Edit]

First Name: [Edit]

Address: [Edit]
[Edit]

City: [Edit]

State: [Edit]  Zip: [Edit]

Phone: [Edit]

Phone: [Edit]

Phone: [Edit]

Schedule Details

Patient ID: [Edit]

Last Name: [Edit]

First Name: [Edit]

Date: [Edit]

Time: [Edit]

Visit Description:

*Para*

First Time

Were cases committed?  ◉ Yes  ◉ No

If yes,

How many? [Edit]

When can we expect the demographics? [Edit]

If no,

Why? [Edit]

[Prev] [Next]

FIG. 79

Follow-up

Did the follow up yield cases?  ◉ Yes  ◉ No

Is an additional follow up required?  ◉ Yes  ◉ No

If yes,
  When? [Edit]
  What do they need? [Edit]

[Prev] [Next]

FIG. 80

Follow-up

Did you get the cases?  ◉ Yes  ◉ No

If yes,

When?  [Edit]

How many potential cases?  [Edit]

[Prev] [Next]

FIG. 81

Cyclic

Is the practice currently reffering cases?  ● Yes  ● No

What was the point of the visit?  [Edit]

Who did you speak with?
● MD
● RN          Name: [Edit]
● Other

What was the result?
● Positive
● Negative    Reason: [Edit]
● Unchanged

[Prev] [Next]

FIG. 82

SYSTEM AND METHOD FOR REMOTE PATIENT MONITORING AND ASSESSMENT TO FACILITATE PATIENT TREATMENT

BACKGROUND OF THE INVENTION

1. Field of the Invention

The present invention relates to a system and method for remote patient monitoring and assessment to facilitate patient treatment.

2. Related Art

In the healthcare field, it is important to monitor and assess patients. This is particularly the case where patients are not mobile and caregivers visit patients. In such circumstances, it is also important that treatment given, to patients by caregivers is documented and reviewed to ensure that patients are given appropriate treatment. This need is particularly prevalent in the field of in-home patient care, where medical personnel travel to a patient's residence to administer care. For example, patients having implanted infusion pumps are often visited at their homes by in-home caregivers so that they can perform various caregiving tasks, such as inspecting and treating implantation sites on patients' bodies, refilling drugs to be delivered by the infusion pump, and observing the patient's physical (as well as mental) condition. Since the care provided by these medical personnel is very important to the patient's health and safety, it is critical that the care provided is adequately monitored by appropriate personnel.

It is known in the art to provide portable, hand-held computer systems for use by medical personnel in recording patient medical information. In such systems, a nurse or other medical practitioner uses the hand-held computer system to record patient vital signs, observed conditions, etc. The data gathered by such systems can be transmitted to a central computer system (e.g., a server), where it can be electronically processed for storage as part of a patient's digital medical record, and/or printed or accessed electronically by a doctor or other medical personnel. Such systems are primarily used for data storage and do-not-provide real-time controls on the quality of care provided by the medical personnel.

SUMMARY OF THE INVENTION

A system and method for remote patient monitoring and assessment to facilitate patient treatment, and for caregiver monitoring, is provided. In one aspect, the system includes at least one portable computing device operated by a caregiver. The at least one portable computing device generates a plurality of user interface screens for allowing the caregiver to enter information relating to a patient's medical condition and to treatment of the patient by the caregiver. The portable computing device includes means for comparing a parameter of the information entered by the caregiver to a pre-defined threshold to determine whether the parameter is acceptable. The portable computing device also includes means for generating and displaying an alert screen on the portable computing device if the means for comparing the parameter determines that the parameter is unacceptable. The alert screen may display a corrective action to be taken by the caregiver. The system further includes a central server in communication with the portable computing device via a network, the central server receiving the information entered by the caregiver and electronically generating a report summarizing the patient's medical condition and treatment given to the patient by the caregiver, and means for transmitting the report to a recipient.

In another aspect, a method for remotely monitoring and assessing a patient to facilitate patient treatment is provided, and includes the steps of providing a portable computing device to a caregiver, displaying a plurality of user interface screens on the portable computing device, allowing the caregiver to enter information relating to a patient's medical condition and to treatment of the patient using the plurality of user interface screens on the portable computing device, transmitting the information entered by the caregiver to a central server in communication with the portable computing device, the central server electronically generating a report summarizing the patient's medical condition and treatment given to the patient by the caregiver, comparing a parameter of the information entered by the caregiver to a pre-defined threshold to determine whether the parameter is acceptable, and displaying an alert screen on the portable computing device. The alert screen may include a corrective action to be taken by the caregiver if the parameter is unacceptable.

In another aspect, the system and method for remote patient monitoring and assessment includes a computer-readable storage medium having computer-readable instructions for remotely monitoring and assessing a patient to facilitate patient treatment. The computer-readable instructions, when executed by a portable computing device operated by a caregiver, cause the portable computing device to execute the steps of displaying a plurality of user interface screens on the portable computing device, allowing the caregiver to enter information relating to a patient's medical condition and treatment of the patient using the plurality of user interface screens on the portable computing device, transmitting the information entered by the caregiver to a central server in communication with the portable computing device, for subsequent electronic generation of a report summarizing the patient's medical condition and treatment given to the patient by the caregiver, comparing a parameter of the information entered by the caregiver to a pre-defined threshold to determine whether the parameter is acceptable, and displaying an alert screen on the portable computing device. The alert screen may include a corrective action to be taken by the caregiver if the parameter is unacceptable.

In another aspect, a method for remotely monitoring and assessing a patient having an implanted infusion pump to facilitate patient treatment is provided, and includes the steps of providing a portable computing device to a caregiver, displaying a plurality of user interface screens on the portable computing device, allowing the caregiver to enter information relating to the implanted infusion pump using the plurality of user interface screens on the portable computing device, comparing a parameter of the information entered by the caregiver to a pre-defined threshold to determine whether the parameter is acceptable, displaying an alert screen on the portable computing device if the parameter is unacceptable, and allowing the caregiver to refill the implanted infusion pump if the parameter is acceptable.

In another aspect, a method for remotely monitoring and assessing a patient having an implanted infusion pump to facilitate patient treatment is provided, and includes the steps of providing a portable computing device to a caregiver, allowing the caregiver to withdraw fluid remaining in the implanted infusion pump, displaying a plurality of user interface screens on the portable computing device, allowing the caregiver to enter information relating to the fluid withdrawn from the implanted infusion pump using the plurality of user interface screens on the portable computing device, analyzing the information entered by the caregiver, comparing the information to an expected amount of remaining fluid, and displaying an alert screen on the portable computing device if the information entered by the caregiver does not match the expected amount of remaining fluid.

BRIEF DESCRIPTION OF THE DRAWINGS

The foregoing features of the patient monitoring and assessment system will be apparent from the following Detailed Description of the Invention, taken in connection with the accompanying drawings, in which:

FIGS. 8-82 are screenshot showing various user interface screens generated by the smart telephone of the patient monitoring and assessment system for allowing caregivers to capture a plethora of information relating to in-home care of a patient.

DETAILED DESCRIPTION OF THE INVENTION

The system and method for remote patient monitoring and assessment is discussed in detail below, with reference to FIGS. 1-82. The system of the present invention provides a field-operable, remotely-monitored caregiver and patient assessment system which includes a central server in communication with a plurality of smart cellular telephones having local user interface screens for capturing treatment information, and a built-in alerting feature which alerts a caregiver as to an incorrect treatment parameter (e.g., an incorrect dosage for a patient, based upon dosage information input by the caregiver). The system provides caregivers with immediate access to supervisory personnel in the event that an issue arises while the caregiver is at the patient's location. In so doing, the system allows for not only the remote assessment of patients, but also remote oversight of caregiver activities. Further, the information acquired by the present invention can be used for marketing purposes, e.g., by a pharmaceutical company to focus future marketing efforts directed to medical personnel and/or to patients.

Figure 1:
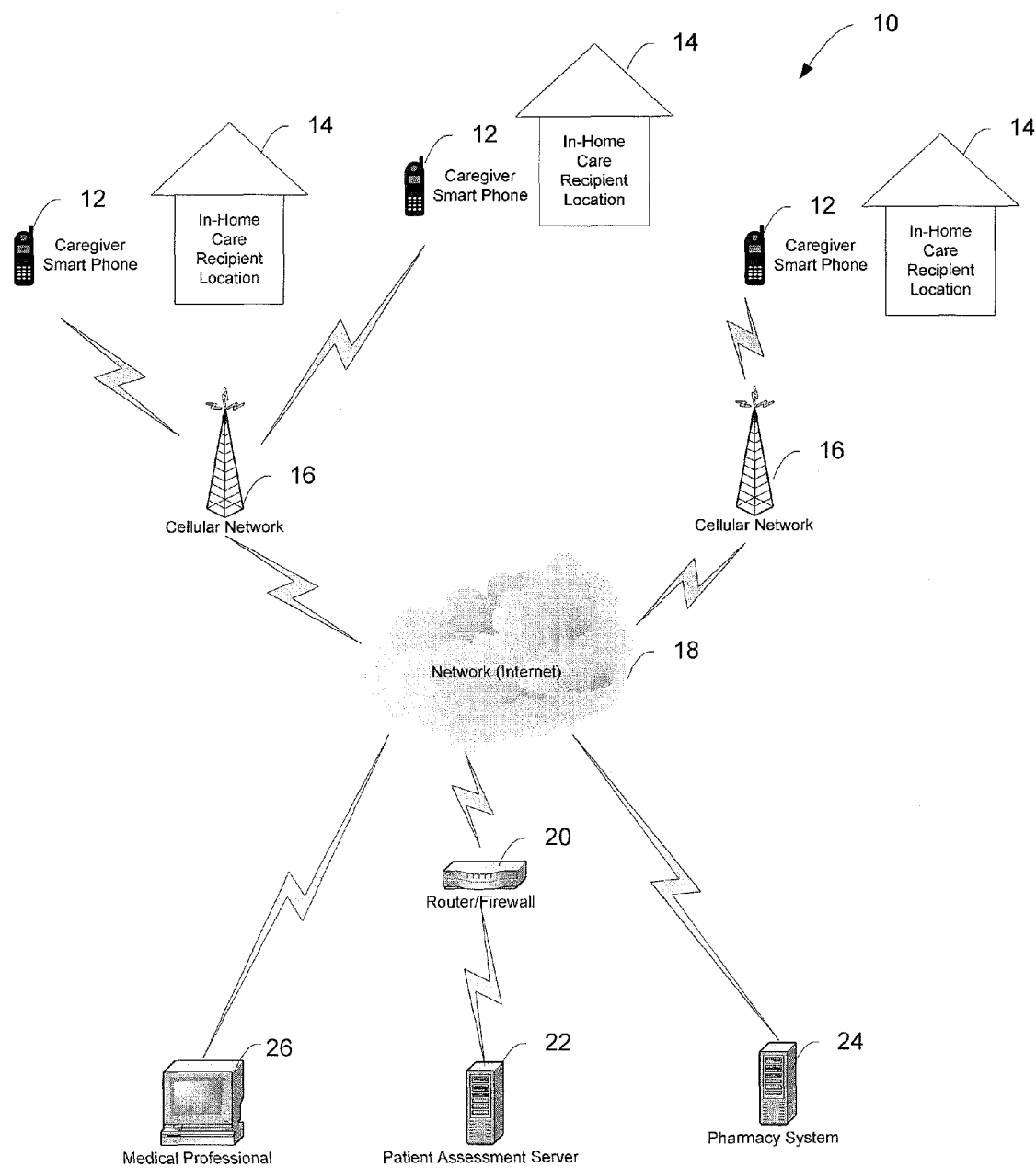
FIG. 1 is a diagram showing the patient monitoring and assessment system.

FIG. 1 is a diagram showing the system 10 for remote patient monitoring and assessment. The system 10 includes a plurality of portable computing devices, such as "smart" cellular telephones 12 operated by caregivers (e.g., nurses employed by a home nursing service, home infusion care service, etc.). The caregivers provide in-home care to patients in their residences 14, and carry the smart phones 12 with them. The smart phones 12 each execute a local assessment software application/engine (discussed in greater detail below), which obtains information from each caregiver relating to the patient's medical condition and to treatment provided to the in-home patient by the caregiver, to allow for remote monitoring and assessment of the caregiver's services as well as to remotely monitor and assess the in-home patient's condition. The smart phones 12 could be any suitable smart cellular telephones (such as the HTC Fuze® smart phone, a Blackberry® smart phone, iPhone® smart phone, etc.) which operate a suitable operating system and have both a graphical user interface and Internet connectivity. Preferably, the smart phones 12 operate the Windows Mobile operating system, but of course, other operating systems could be used. The smart phones 12 communicate with one or more cellular networks 16, which provide voice and Internet connectivity for the smart phones 12 using any suitable communications protocol, such as 3G, 4G, CDMA, 1XRTT, EVDO, GSM, GPRS. Also, the smart phones 12 could communicate directly with the Internet using a suitable local wireless network, such as a WiFi (IEEE 802.11) or WiMax wireless data network. It is also noted that the smart phone 12 could be substituted with portable computing devices not having telephone capabilities, such as personal digital assistants (PDAs), handheld computers, laptop computers, etc.

The cellular network(s) 16 communicate with a data network 18, such as the Internet, a corporate WAN, a campus network, a metropolitan area network (MAN), etc. Also communicating with the network 18 are a patient assessment server 22 (e.g., via suitable communications equipment such as router 20) and, optionally, a pharmacy system 24 and a computer system 26 operated by a medical professional (e.g., doctor, nurse, therapist, etc.). The patient assessment server 22 receives information captured by the smart phones 12 relating to patients' medical conditions and to the caregivers' in-home treatment of patients, for remote monitoring and assessment of the patient as well as caregiver's performance. It is noted that the system 10 could also be used at any location, including a single location, such as a hospital, nursing home, etc., for patient monitoring and assessment. In such circumstances, the patients and caregivers need not be remote from the patient assessment server 22, but rather, could be located at or near the same location as the patient assessment server 22. Additionally, the system 10 could be used at a doctor's office, at a nursing home, or at a healthcare facility, to monitor and assess patient treatment. Further, the system 10 could be used to identify ("double-check") whether a given person is a drug seeker who should not receive drugs.

It is noted the system 10 allows for remote monitoring and assessment of in-home treatments of patients having implanted medical devices, such as infusion pumps. Such pumps infuse fluids into a patient's circulatory system, such as medications and/or nutrients. They can infuse fluids continuously, intermittently, or in response to patient demand. Implanted infusion pumps must be periodically refilled, and the process for refilling such pumps typically involves inserting a syringe through the skin and into a reservoir of the pump, and refilling the reservoir using the syringe. One example of an implanted infusion pump is the SYN-CHROMED II pump manufactured by Medtronic, Inc., which is available with a 20 mL or 40 mL reservoir. Of course, the present invention could be utilized to monitor other types of medical equipment utilized by a patient, and is not limited to infusion pump monitoring and assessment.

Figure 2:
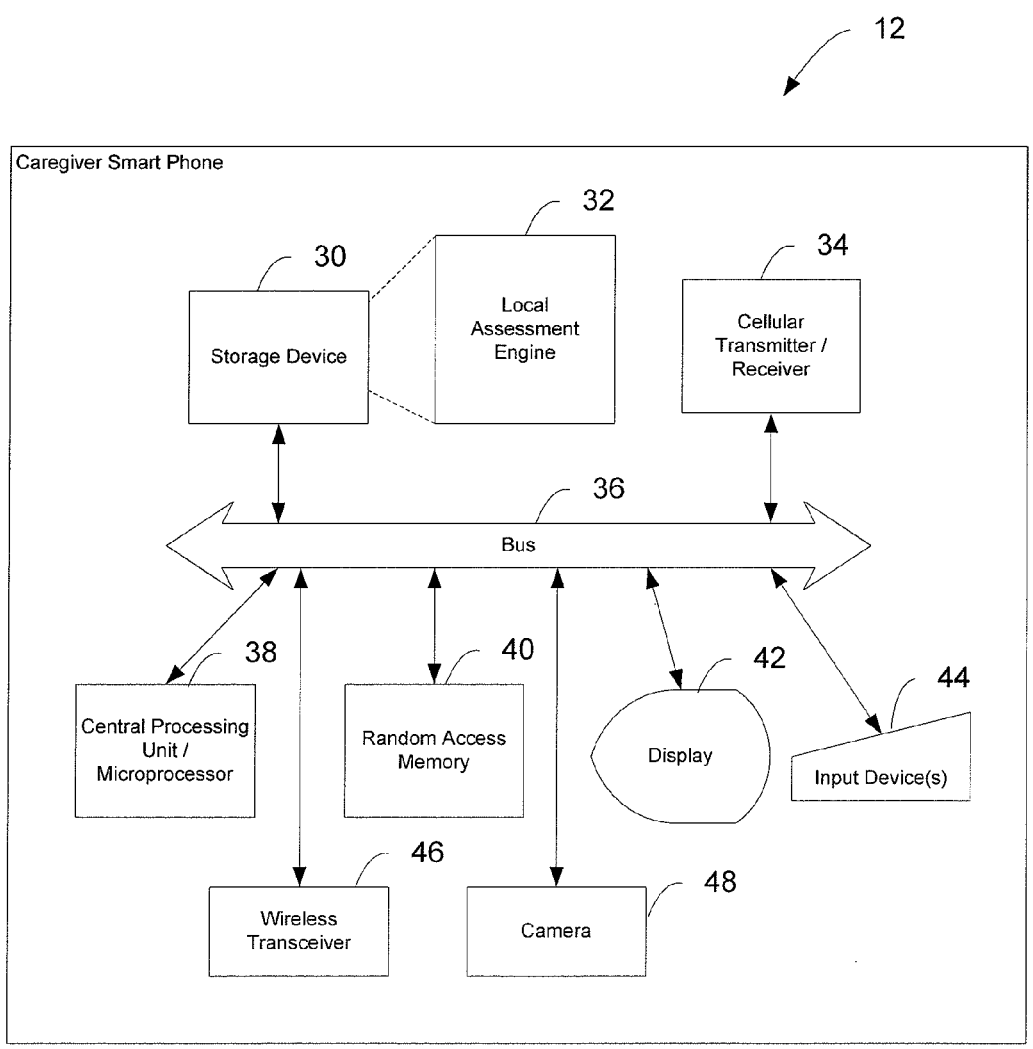
FIG. 2 is a diagram showing hardware and software/firmware components of a smart telephone utilized by a caregiver in the patient monitoring and assessment system.

FIG. 2 is block diagram showing hardware and software/firmware components of the smart phones 12 of FIG. 1 in greater detail. The phones 12 each include a non-volatile storage device 30 which stores a local assessment software module 32 (which provides user interface screens for permitting caregivers to enter information about in-home treatment procedures, patient information, etc., as discussed in greater detail below), a cellular transmitter/receiver 34, a bus 36, a central processing unit/microprocessor 38, a random access memory 40, a display 42, one or more input devices 44, an optional wireless transceiver 46, and an optional camera 48. The storage device 30 could comprise any suitable, non-volatile, computer-readable storage medium capable of storing the local assessment engine 32 of the system and method for remotely monitoring and assessing patients, such a disk and/or non-volatile memory (e.g., read-only memory (ROM), eraseable, programmable ROM (EPROM), electrically-eraseable, programmable ROM (EEPROM), flash memory, field-programmable gate array (FPGA), etc.). The cellular transmitter/receiver 34 could include any suitable type of transmitter/receiver capable of allowing the smart phone 12 to communicate with a cellular network (e.g., 3G or 4G transceiver, etc.). The central processing unit 38 could include any suitable single- or multiple-core microprocessor of any suitable architecture, such as the Qualcomm® MSM7201A RISC microprocessor or any other suitable microprocessor. The random access memory 40 could include any suitable, high-speed, random access memory typical of most modern computers, such as dynamic RAM (DRAM), etc. The display 42 could be any suitable computer display, such as a liquid crystal display (LCD), touchscreen, etc. The input device 44 could be any suitable user input device, such as a keyboard, mouse, touchpad, touchscreen, trackball, scroll wheel, etc. The optional wireless transceiver 46 could be a WiFi a WiMax transceiver, a BlueTooth® transceiver, or any other type of wireless network transceiver. The camera 48 could be an on-board digital camera such as those commonly provided in cellular telephones.

Figure 3:
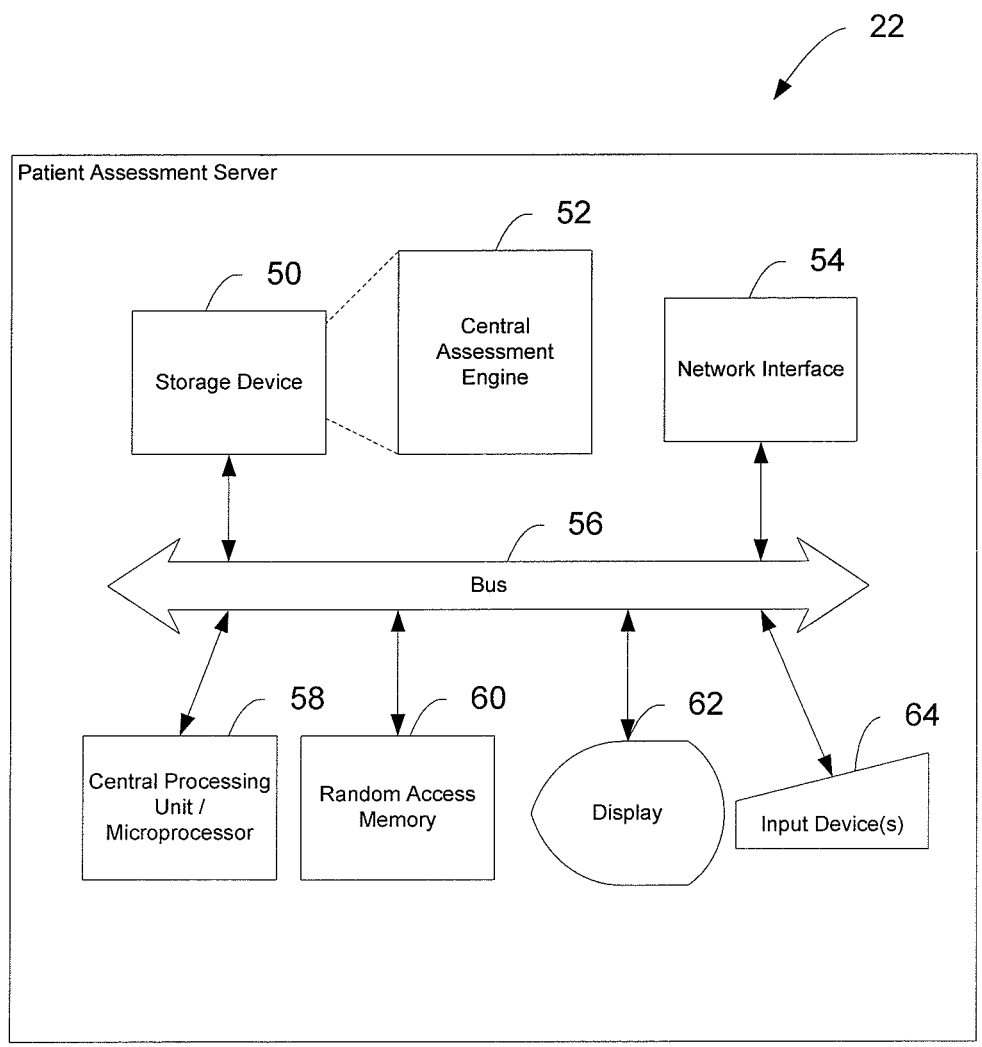
FIG. 3 is a diagram showing hardware and/or firmware components of a central patient assessment system, which communicates with one or more caregiver-operated smart telephones.

FIG. 3 is block diagram showing hardware and software/firmware components of the patient assessment server 22 of FIG. 1 in greater detail. The server 22 includes a non-volatile storage device 50 which stores a central assessment software module 32 (which gathers information transmitted to the server 22 from each caregiver's smart phone 12 and prepares customized reports, as discussed in greater detail below), a network interface 54, a bus 56, a central processing unit/microprocessor 58, a random access memory 60, a display 62, and one or more input devices 64. The storage device 50 could comprise any suitable, non-volatile, computer-readable storage medium capable of storing the central assessment engine 52 of the system and method for remotely monitoring and assessing patients, such a disk and/or non-volatile memory (e.g., read-only memory (ROM), eraseable, programmable ROM (EPROM), electrically-eraseable, programmable ROM (EEPROM), flash memory, field-programmable gate array (FPGA), etc.). The network interface 54 could include any suitable type of wired or wireless transceiver; such as an Ethernet transceiver, WiFi transceiver, etc. The central processing unit 58 could include any suitable single- or multiple-core microprocessor of any suitable architecture, such as an Intel microprocessor or any other suitable microprocessor. The random access memory 60 could include any suitable, high-speed, random access memory typical of most modern computers, such as dynamic RAM (DRAM), etc. The display 62 could be any suitable computer display, such as a liquid crystal display (LCD), touchscreen, cathode ray tube (CRT), etc. The input device 64 could be any suitable user input device, such as a keyboard, mouse, touchpad, touchscreen, trackball, scroll wheel, etc. It is noted that the server 22 need to be a single server, but rather, could comprise one or networked computing systems, "cloud" computing environment, etc.

Figure 4:
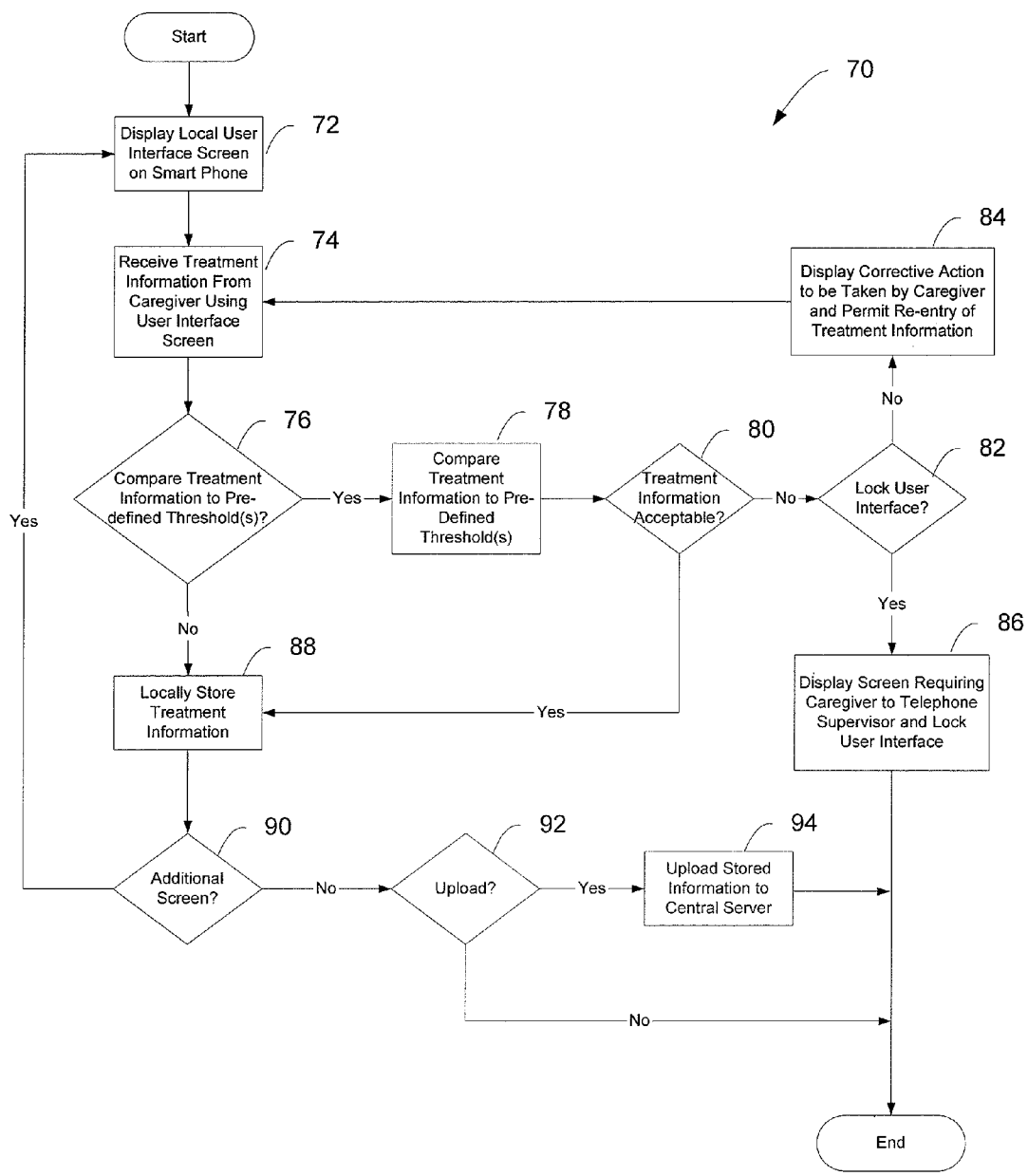
FIGS. 4-7 are flowcharts showing processing steps carried out by the patient monitoring and assessment system.

FIG. 4 is flowchart showing processing steps, indicated generally at 70, carried out by the patient monitoring and assessment system. The processing steps 70 are carried out by the local assessment engine 32 of FIG. 2. Beginning in step 72, the local assessment engine 32 displays one or more user interface screens on the smart phone 12 operated by a caregiver. Such screens are discussed in further detail below in connection with FIGS. 8-82. The screens allow a caregiver to input numerous types of information relating to a patient's medical condition, as well as in-home treatment of a patient. In step 74, the system receives information from the caregiver using the user interface screen(s). In step 76, a determination is made as to whether the information entered by the caregiver is to be compared to pre-determined thresholds. If a positive determination is made, step 78 occurs, wherein the treatment information is compared to the pre-determined threshold. Then, in step 80, a decision is made as to whether the treatment information entered by the caregiver is acceptable. If so, step 88 occurs. Otherwise, step 82 occurs, wherein a determination is made as to whether to lock the user interface of the caregiver's smart phone. If a negative determination is made, step 84 occurs, wherein an alert screen is displayed to the caregiver, and, optionally, a corrective action to be taken by the caregiver is displayed on the screen of the smart phone. Control then returns to step 74. If, in step 82, a determination is made to lock the user interface, step 86 occurs, wherein the screen of the caregiver's smart phone is locked and a screen is displayed requiring the caregiver to place a telephone call to his/her supervisor in order to continue.

Advantageously, the steps 76-86 permit the system and method for remotely monitoring and assessing patients to remotely monitor and determine whether the caregiver is giving a correct treatment to patient, in real or near-real time. For example, a screen could be displayed requiring the caregiver to input information about a drug name and dosage size of a pharmaceutical product to be given to an in-home infusion patient. The information supplied by the caregiver is then compared to pre-determined thresholds, and if the information is not acceptable, the caregiver's smart phone could either display a corrective screen or the entire phone could be locked. Such a feature could assist in preventing potentially dangerous and/or lethal dosages from being accidentally given to a patient. Also, the system could be programmed to calculate an acceptable range for a given parameter (e.g., an acceptable dosage range for a given drug), and if the information provided by the caregiver about the parameter falls within the calculated acceptable range, the system could permit the caregiver to continue administering care. Otherwise, if the information is not within the calculated acceptable range, the system could generate an alert screen, and/or could lock the smart phone and require the caregiver to telephone his/her supervisor.

Additionally, the system could be programmed to display a screen which allows a caregiver to provide information about an amount of fluid remaining in an implanted infusion pump in a patient, after the caregiver has withdrawn the remaining fluid from the implanted infusion pump (e.g., using a syringe). Once the information has been entered, the system could analyze the information and compare the information to a pre-defined expected remaining amount. If the information does not match the expected remaining amount, the system could display an alert screen. The system could also calculate a range of expected remaining amounts, and could compare the information to the range. If the information is outside of the range, the system could display an alert screen.

In step 88, the local assessment engine locally stores treatment information entered by the caregiver in a memory of the smart phone (e.g., in a local database running on the smart phone). Then, in step 90, a determination is made as to whether an additional user interface screen is to be displayed to the user (e.g., to allow the user to enter additional information). If so, control returns to step 72 so that additional screens can be displayed. Otherwise, step 92 occurs, wherein a determination is made as to whether to transmit the stored information entered by the user. If a negative determination is made, processing ends. Otherwise, step 94 occurs, wherein the stored information is uploaded to the caregiver assessment server 22 of FIG. 1. It is noted that the stored information could be transmitted from the smart phones 12 to the server 22 continuously (e.g., in real time), periodically, or at a pre-defined time. Information could be uploaded to the caregiver assessment server 22 using file transfer protocol (FTP), and uploaded information could be stored in a suitable directory structure. For example, a unique folder could be created on the server 22 corresponding to a smart phone, and information could be transmitted to that folder via FTP. The uploaded information could then be formatted so that it can be accessed by a suitable, commercially-available patient data management software package, such as the CPR+ software package produced by Definitive Homecare Solutions, Ltd.

Figure 5:
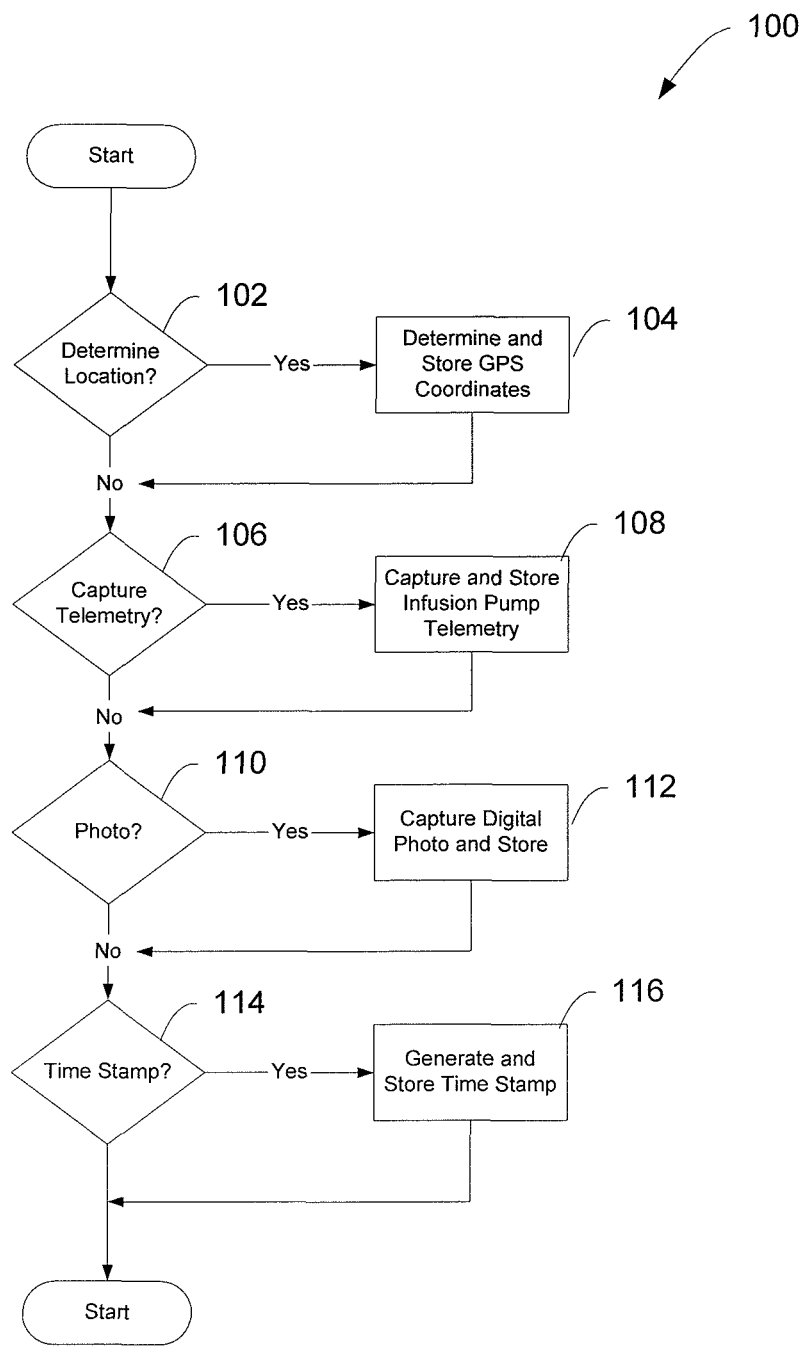

FIG. 5 is flowchart showing additional processing steps (indicated generally at 100) that can be carried out by the local assessment engine 32 of the caregiver smart phone 12. In step 102, a determination is made as to whether the location of the caregiver is to be identified and recorded. If so, step 104 occurs, wherein the GPS coordinates of the phone 12 are determined and stored. The coordinates could be periodically transmitted to the server 22, or immediately transmitted thereto. By tracking the location of the caregiver, the caregiver's supervisor can ascertain whether the caregiver is at the patient's location when he/she should be. It also provides security for the caregiver in the event of an emergency, such that the caregiver's physical location can be quickly ascertained. It is noted that capturing of location information could be programmed to automatically be performed whenever the local assessment software module of the smart phone is launched/opened.

In step 106, a determination is made as to whether to capture telemetry information associated with one or more medical devices being used by the patient, such as telemetry information from an in-home infusion pump or other device. If so, step 108 occurs, wherein the telemetry information is captured by the smart phone 12. Telemetry information could be captured in many ways, including, but not limited to, a photograph of a telemetry information page printed out or displayed by the pump (and taken using the camera 48 of the smart phone 12), wireless transmission of telemetry information from the pump to the smart phone 12 (using the wireless transceiver 46 of the phone 12 and a wireless communications link established between the smart phone 12 and the pump, such as a WiFi link, Bluetooth link, etc.), or by manual input of telemetry information by the caregiver into a user interface screen generated by the smart phone 12. Once the telemetry information has been captured, it can be stored locally on the phone 12 for subsequent transmission to the server 22, or immediately transmitted to the server 22.

In step 110, a determination is made as to whether a photo is to be taken of a patient's body. For example, a photo could be taken of a wound site, an entry site for tubing of the infusion pump, etc. If so, step 112 occurs, wherein the caregiver takes a photo using the camera 48 of the phone 12. The photo can be stored locally on the phone 12 for subsequent transmission to the server 22, or it can be immediately transmitted to the server 22.

In step 114, a determination is made as to whether one or more time stamps should be generated. For example, a time stamp could be used to gauge how long a caregiver has been treating a patient, thereby providing an indication of the quality of care that the patient receives. The time stamp could indicate the amount of time that has elapsed between launching/opening of the local assessment software module on the caregiver's smart phone to completion of data entry by the caregiver. If a positive determination is made in step 114, step 116 occurs, wherein the current time is determined (e.g., by an internal clock of the smart phone 12) and a time stamp is generated and stored for subsequent transmission to the server 22, immediate transmission thereto, or for storage as part of a patient's treatment record.

Figure 6:
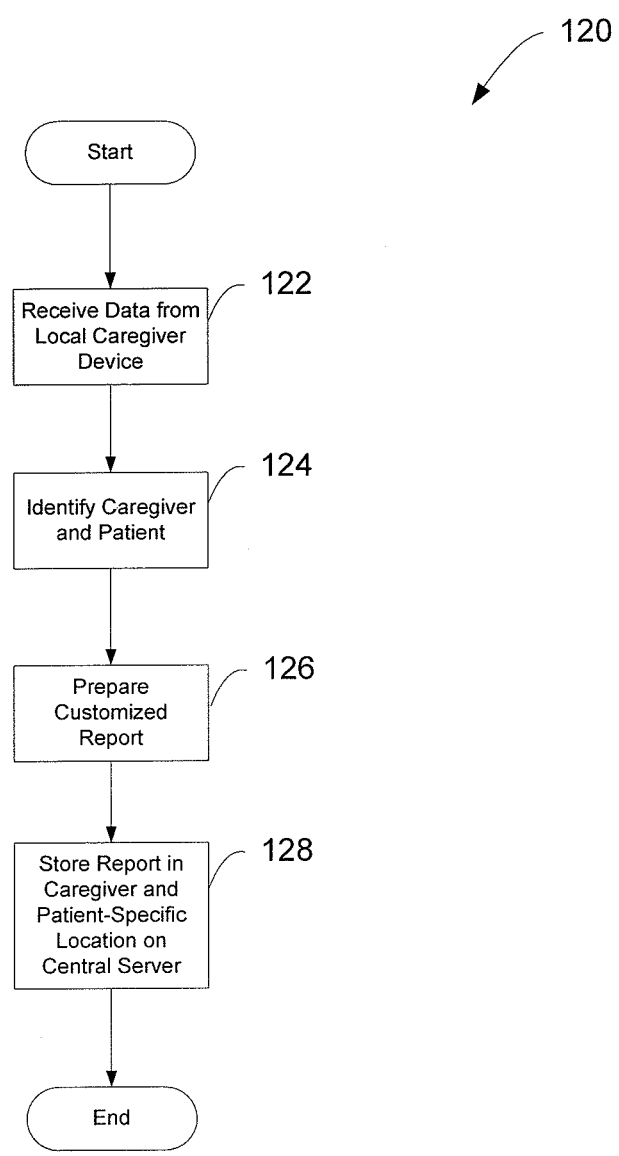

FIG. 6 is a flowchart showing processing steps, indicated generally at 120, performed by the central assessment engine 52 of FIG. 3. The central assessment engine 52 receives, processes, and organizes information transmitted to the server 22 by the caregiver smart phones 12, including information entered by the caregivers using the various user interface screens generated by the system and method for remotely monitoring and assessing patients. It also generates customized reports which can be printed, e-mailed, faxed, and/or accessed via the Internet by any individual having a need to review a patient's in-home care, such as a doctor, nursing supervisor, or other healthcare professional. In step 122, the server 22 receives data from each smart phone 12. As mentioned above, the data could be transmitted periodically, or in real time. In step 124, the caregiver who supplied the information, and the patient to whom the caregiver has been assigned, are identified. Then, in step 126, a customized report is prepared for each patient. The customized report can contain all of the information entered remotely by the caregiver, or only selected portions of interest. In step 128, the report is stored in a caregiver- and patient-specific location on the caregiver assessment server 22. Preferably, the data is stored in such a way as to comply with U.S. laws (e.g., HIPAA regulations) relating to patient data. For example, information for each patient could be stored in database tables or directory structures which are assigned only to one patient, thereby isolating each patient's healthcare data.

Figure 7:
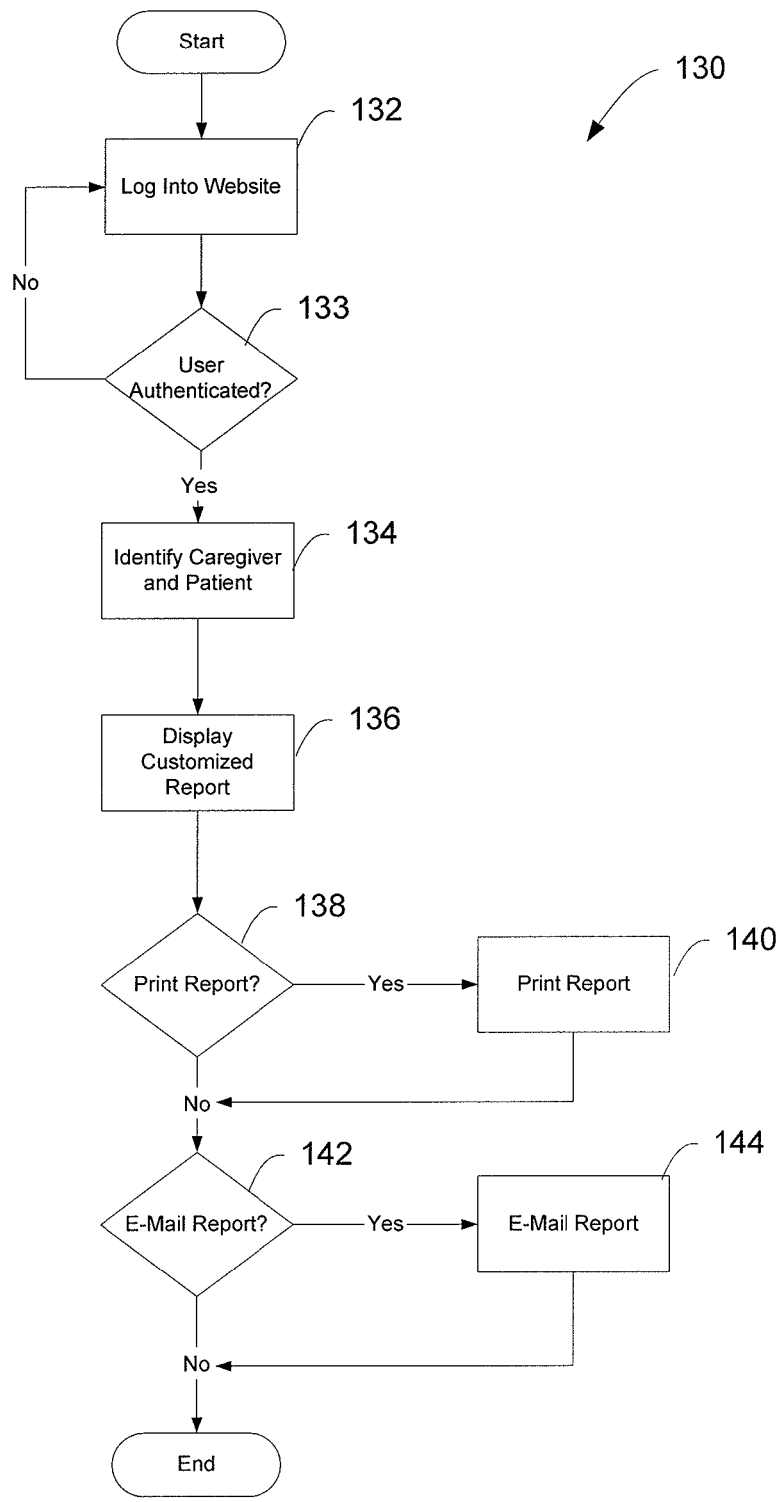

FIG. 7 is a flowchart showing additional processing steps (indicated generally at 130) carried out by the caregiver assessment server 22 for providing reports to users. Beginning in step 132, a user logs onto a website hosted by the assessment server 22 or another server in communication with the assessment server 22. In step 133, a determination is made whether the user is authenticated (e.g., by authenticating the user name and password). If not, control returns to step 132; otherwise control passes to step 134. In step 134, the system prompts the user to identify a desired caregiver and/or a desired patient for whom a report a desired. In step 136, the system obtains the customized report that was previously generated for the patient, and displays the report to the user, e.g., in one or more web browser screens. In such fashion, the user (e.g., a doctor, nurse, manager of a caregiver, etc.) can quickly and conveniently obtain information about a patient's medical condition, in-home treatment, as well as information about the caregiver's performance. In step 138, a determination is made as to whether to print the report. If a positive determination is made, step 140 occurs, wherein the system prints the report for the user, e.g. by sending the report to the user's local printer for printing. In step 142, a determination is made as to whether the report should be e-mailed to the user. If so, step 144 occurs, wherein the report is e-mailed to the user, e.g., as an Adobe® PDF file or in any other suitable format.

It is noted that the reports of the system and method for remotely monitoring and assessing patients could be generated using commercially-available software packages, such as the CPR+ software package produced by Definitive Homecare Solutions, Ltd. It is also noted that the reports generated by the system and method for remotely monitoring and assessing patients could be utilized by pharmaceutical companies for marketing purposes, e.g., to gauge the number of prescriptions of certain drugs that are being written by doctors for in-home care recipients.

Figure 8:
Figure 82:
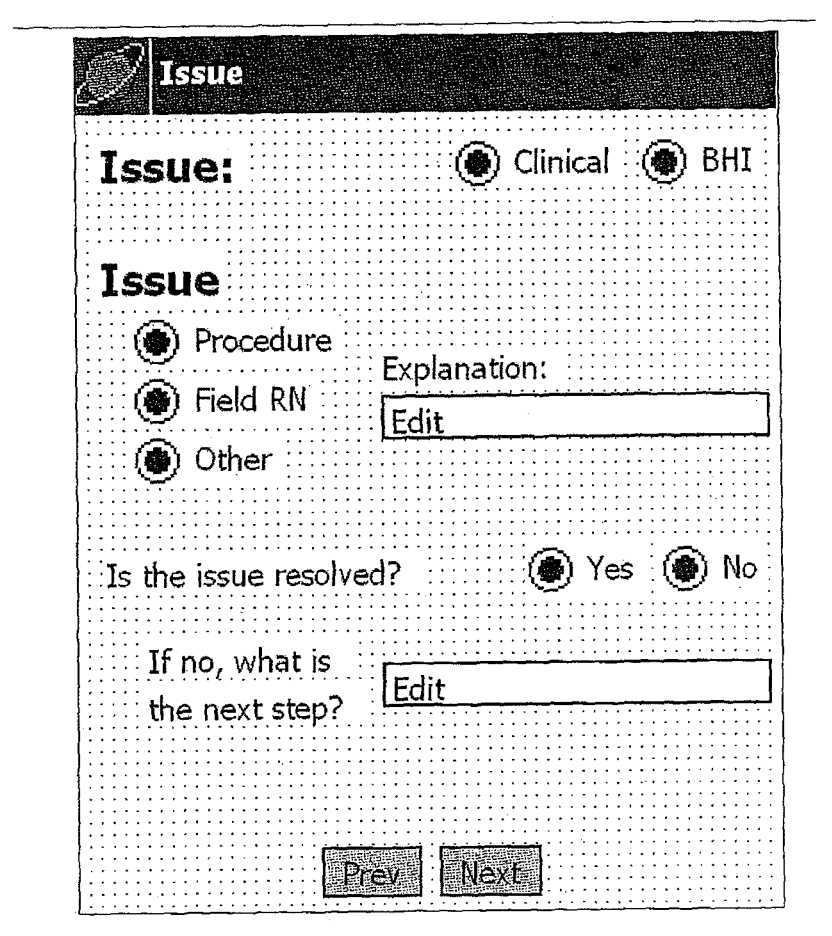

Reference is now made to FIGS. 8-82, which are screenshots showing the various user interface screens generated by the system and method for remotely monitoring and assessing patients, for allowing a caregiver to enter information about a patient's medical condition and in-home treatment of the patient using a smart phone. It is to be understood that the screens shown in FIGS. 8-82 could be varied as desired, and that the invention is not limited to the screens shown and described herein.

FIG. 8 shows an example of a main user interface screen of the system and method for remotely monitoring and assessing patients, which is displayed on the caregiver's smart phone when the system is launched. The main screen allows the user to access patient information screens, appointment scheduling screens, nurse visit screens, marketing visit screens, or exit the system.

Figure 9:

FIG. 9 shows an example of a user interface screen for allowing the caregiver to enter detailed information about a patient being treated. Information that can be captured includes, but is not limited to, patient identifier, patient name, address, telephone number, and allergies that the patient has.

Figure 10:

FIG. 10 shows an example of a user interface screen for allowing the caregiver to enter information about visits that the caregiver has made to the patient's home. Using this screen, the caregiver can create a new entry regarding a visit, edit an existing entry, or delete an existing entry.

Figure 11:
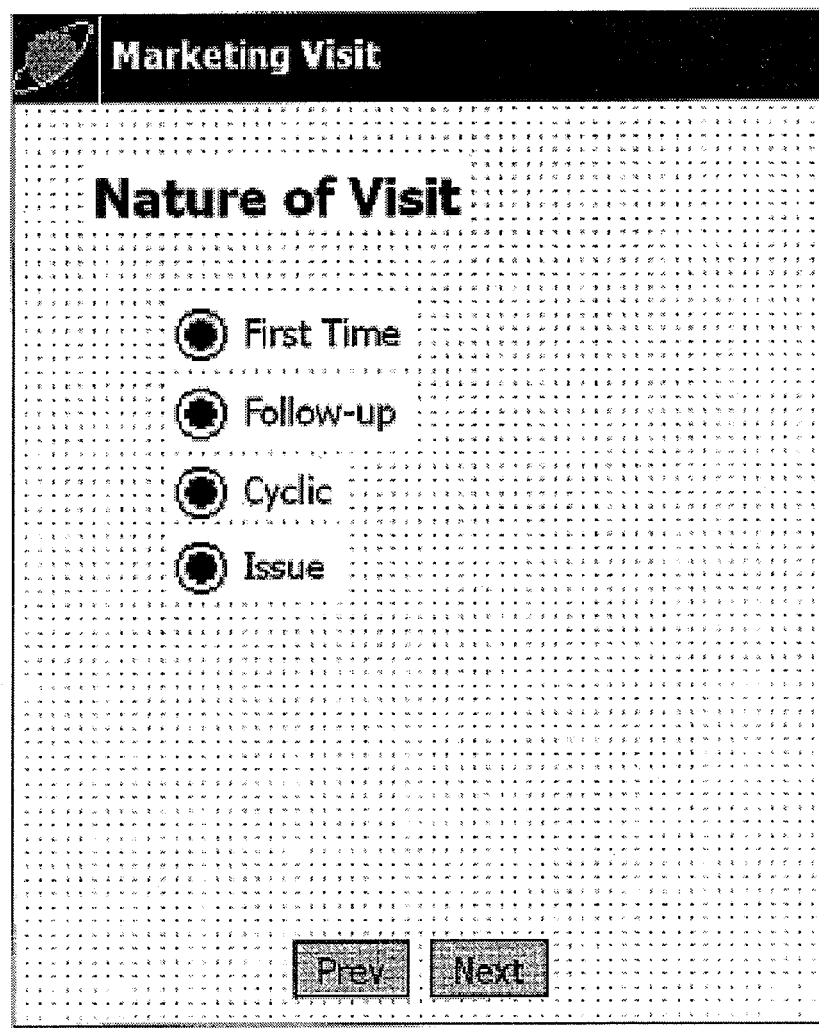

FIG. 11 shows an example of a user interface screen for allowing the caregiver to identify the nature of an in-home visit to a patient. For example, the caregiver can identify the visit as a first-time visit, a follow-up visit, a cyclic (periodic) visit, or a visit pertaining to a specific medial issue that the patient is experiencing.

Figure 12:
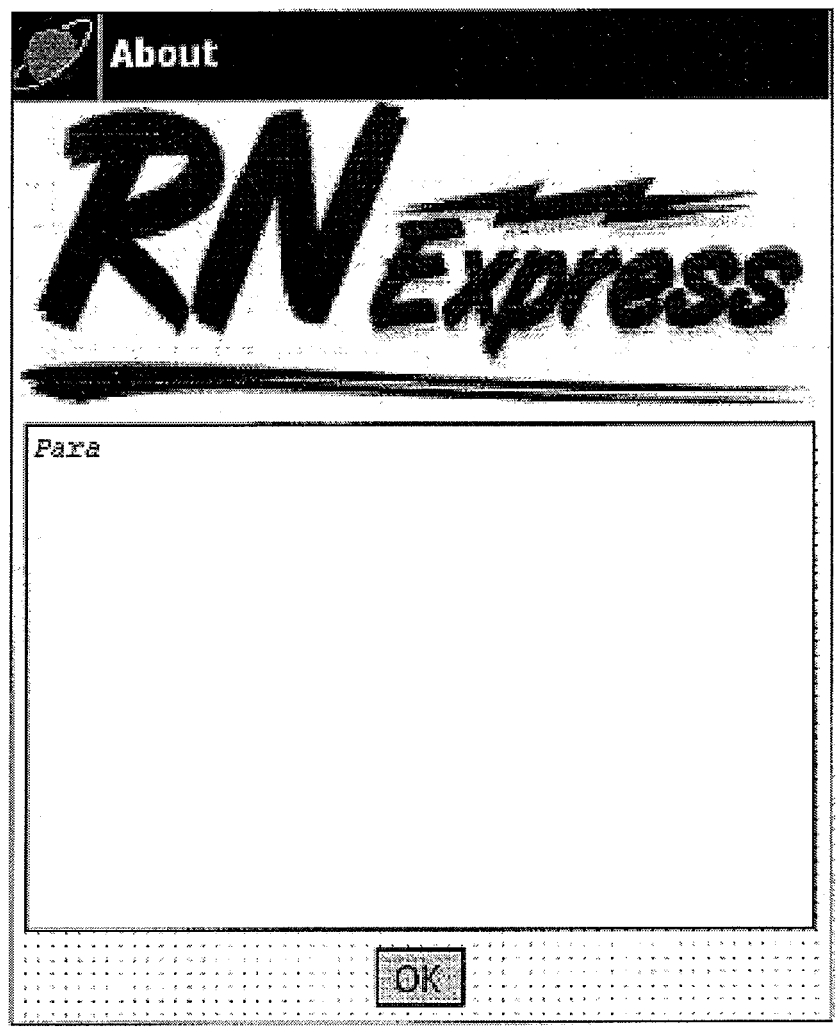

FIG. 12 shows an example of a user interface screen for displaying information about the system itself. This screen could be used by a technician for troubleshooting software components forming part of the system and method for remotely monitoring and assessing patients, determining software versions currently installed on the smart phones, upgrading software versions, etc.

Figure 13:

FIG. 13 show an example of a user interface screen for allowing a caregiver to enter diagnosis information. In this screen, the nurse can indicate whether the in-home patient has impaired mobility, spasticity, increased tone, or pain.

Figure 14:
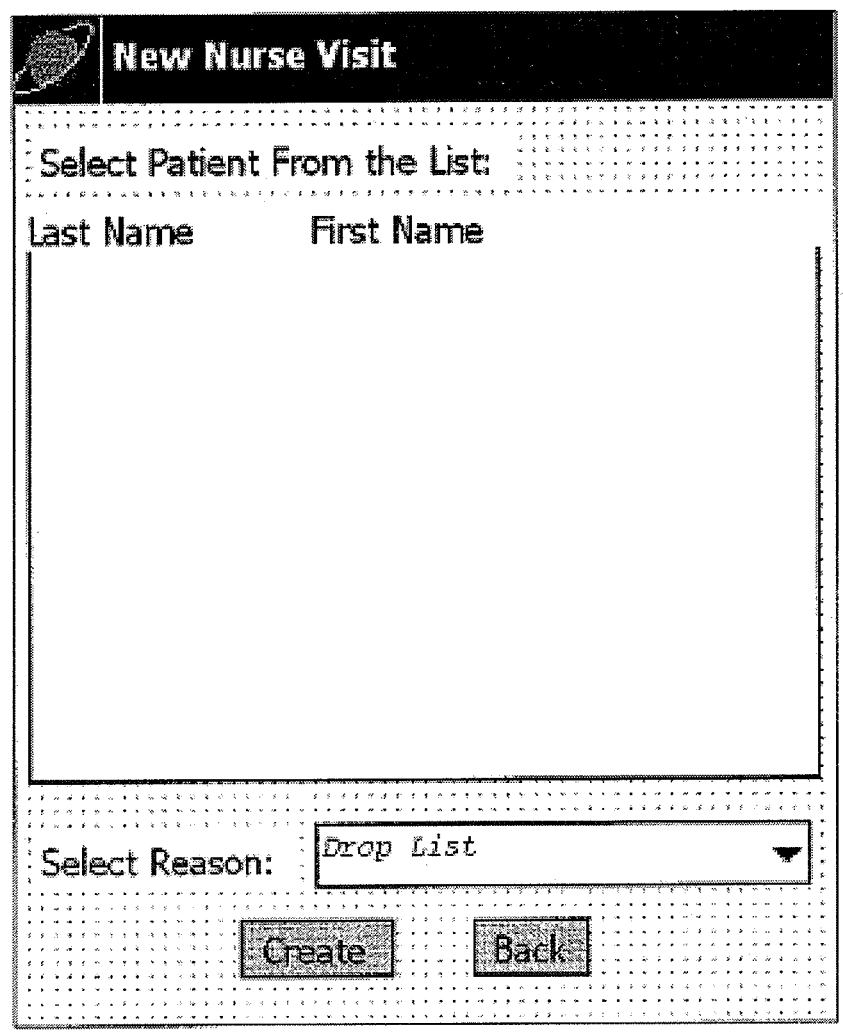

FIG. 14 shows an example of a user interface screen for allowing a caregiver to specify information about a new visit to a patient. Using this screen, the caregiver can select an existing patient from a list and create a new visit entry for the patient. Also, the caregiver can specify a reason for the visit.

Figure 15:

FIG. 15 shows an example of a user interface screen for allowing a caregiver to specify information about a patient's medical history. Examples of the types of information that can be entered include, but are not limited to, hypertension, diabetes, osteoporosis, fractures, cardiac issues, respiratory issues, cancer, infections, immunosuppression, open wounds, prior surgeries, and other information.

Figure 16:
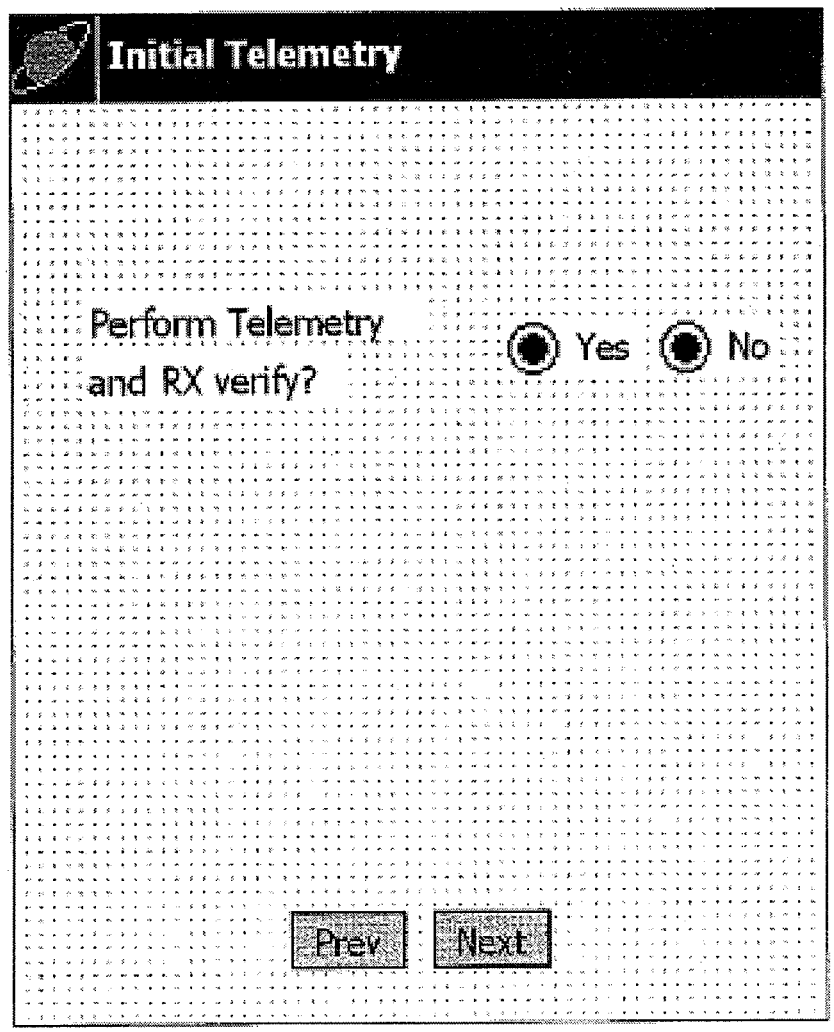

FIG. 16 shows an example of a user interface screen for allowing a caregiver to initiate capturing of information from a medical device being used by a patient, such as an infusion pump. By clicking on the "Perform Telemetry . . . " radio buttons, the user initiates the process of recording telemetry. This process could involve taking a photograph using the camera on the smartphone of a telemetry printout generated by the medical device, which is subsequently (or, immediately) transmitted to the caregiver assessment server. Alternatively, this process could initiate an RF transmission of telemetry directly from the device to the smart phone (e.g., through a Bluetooth® wireless link, etc.). Other processes for obtaining telemetry can also be used.

Figure 17:
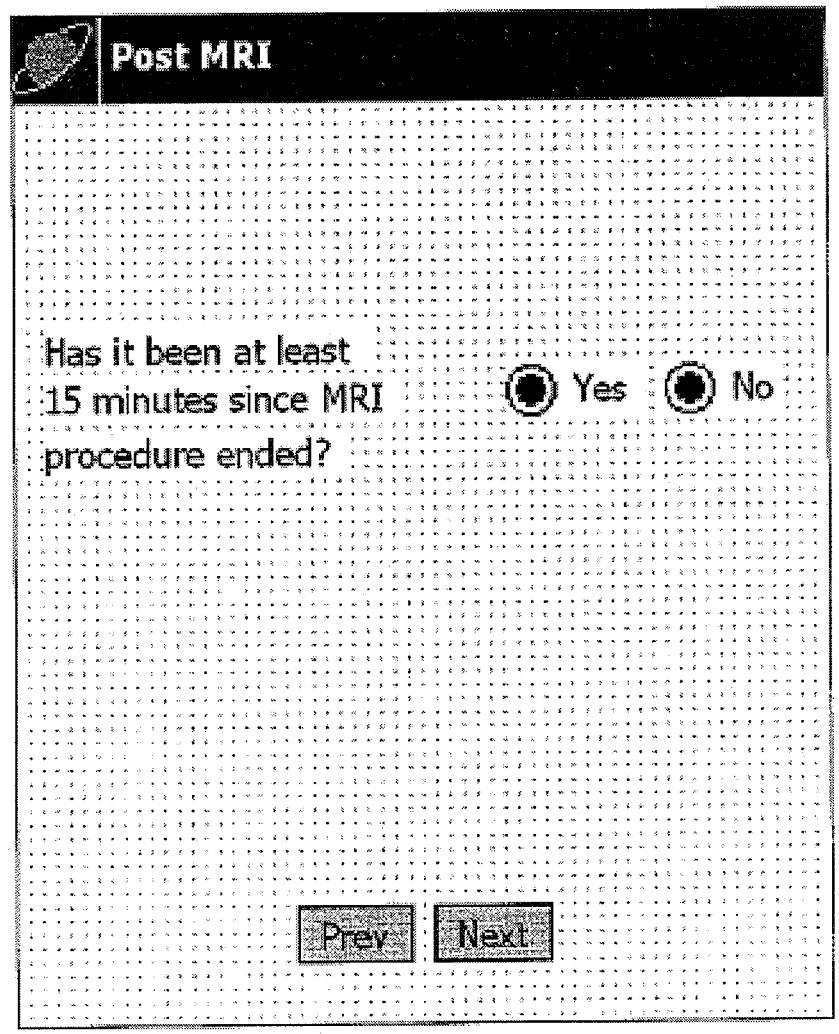

FIG. 17 show an example of a user interface screen for allowing a caregiver to specify information relating to medical scans of the patient, such as MRI scans. For example, in this screen, the caregiver can specify whether a pre-defined amount of time has elapsed since an MRI procedure has been performed on a patient.

Figure 18:
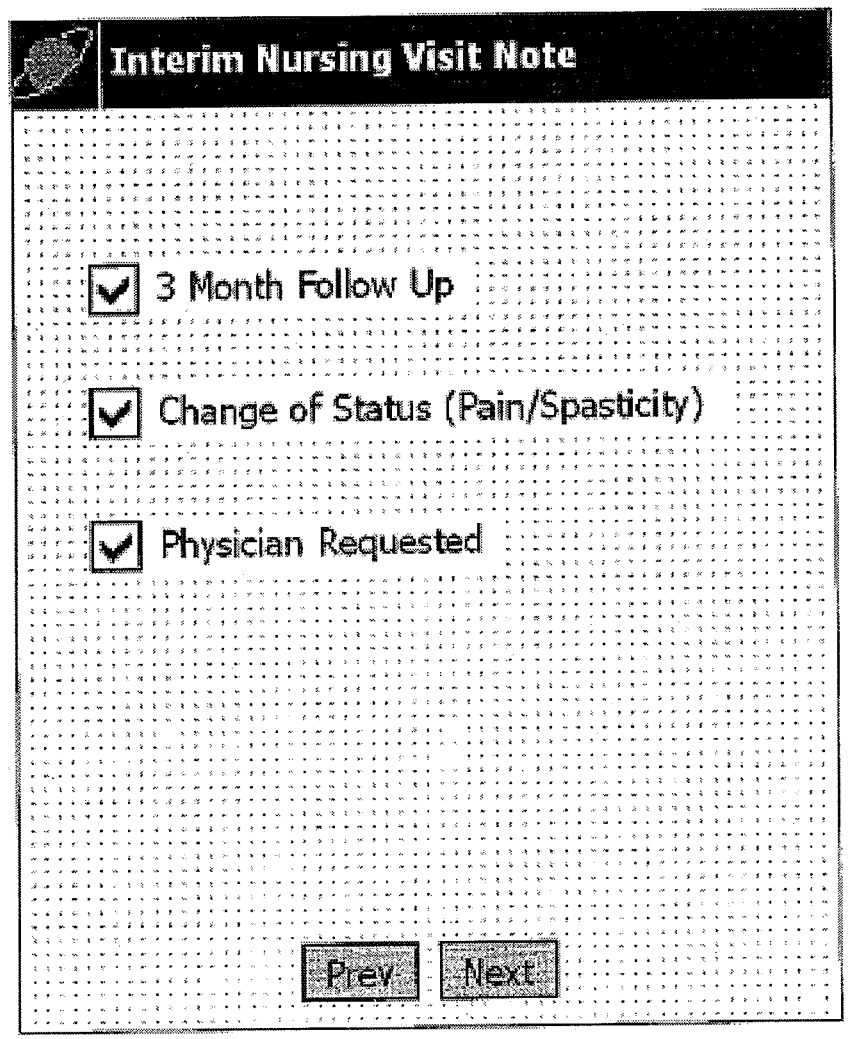

FIG. 18 shows an example of a user interface screen for allowing a caregiver to input information relating to the caregiver's visit. In this screen, the caregiver can specify whether the visit is a periodic (e.g., 3-month) follow-up visit, whether a change in status has occurred with respect to the patient's pain or spasticity, or whether a physician is requested as a result of the visit.

Figure 19:
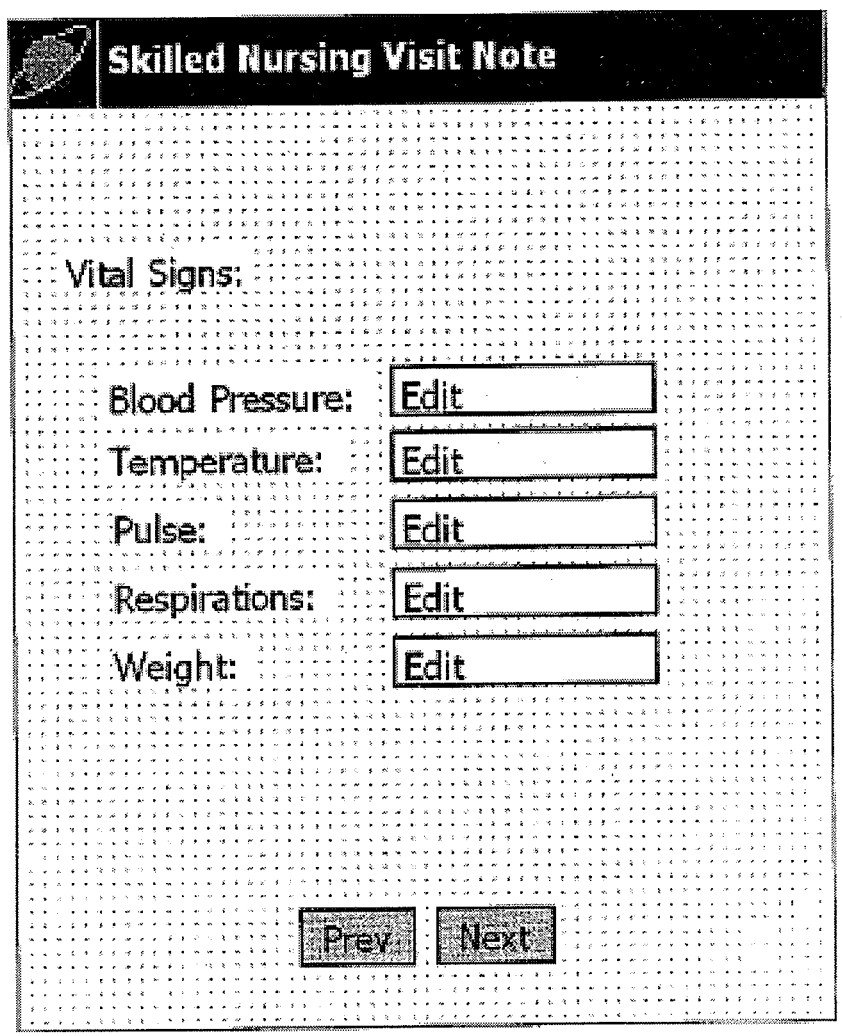

FIG. 19 shows an example of a user interface screen for allowing a caregiver to specify information relating to the patient's vital signs. For example, using this screen, the caregiver can input information relating to the patient's blood pressure, temperature, pulse, respirations, weight, etc.

Figure 20:
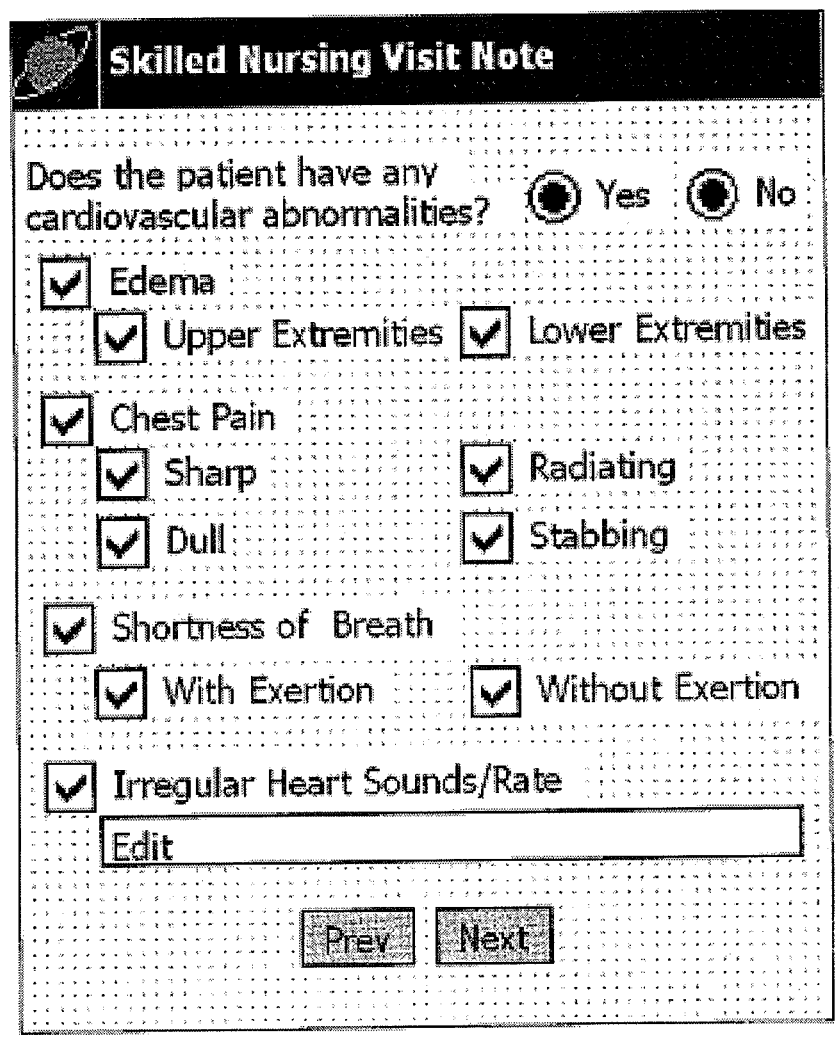

FIG. 20 shows an example of a user interface screen for allowing a caregiver to enter information about the patient's cardiovascular condition. For example, using this screen, the caregiver can input information about whether the patient has cardiovascular abnormalities such as edema in upper and/or lower extremities, chest pain and type of pain, shortness of breath, and irregular heart sounds/rate.

FIG. 21 shows an example of a user interface screen for allowing a caregiver to input information about the patient's airways. In this screen, the caregiver can input information such as whether lung sounds are clear or abnormal (e.g., whether there is wheezing, rhonchi, rales, diminished breath sounds, cough, productive mucous (e.g., thick, thin, green, yellow, clear, etc.)).

Figure 22:

FIG. 22 shows an example of a user interface screen for allowing a caregiver to input information about the patient's digestive function. Examples of information that can be input include whether the patient is experiencing nausea, vomiting, if there are abscent bowel sounds, constipation, date of last bowel movement, diarrhea, or bowel incontinence.

Figure 23:

FIG. 23 shows an example of a user interface screen for allowing a caregiver to input information about the patient's genitourinary function. Examples of information that can be input include whether the patient is experiencing burning, hesitancy, retention, hematuria, foul odor, dark color, incontinence, cloudy urine, etc.

Figure 24:

FIG. 24 shows an example of a user interface screen for allowing a caregiver to enter information about a patient's catheter. In this screen, the caregiver can specify whether the patient has a catheter, and if so, the type of the catheter (e.g., indwelling, Texas, suprapubic, straight catheter, etc.). Also, the caregiver can specify the number of days that the catheter has been in place.

Figure 25:

FIG. 25 shows an example of a user interface screen for allowing a caregiver to input information about wounds that the patient may have. For example, the caregiver can specify whether the patient has any skin breakdowns or wounds, as well as whether the wounds have been treated (and if so, by whom), and other information. Also, using this screen, the user can click on the "Take Picture" button to take a digital picture of the wound (which can be stored on the smart phone and/or transmitted to the caregiver assessment server), or the user can click on the "View Picture" button to view an existing picture of a wound.

Figure 26:
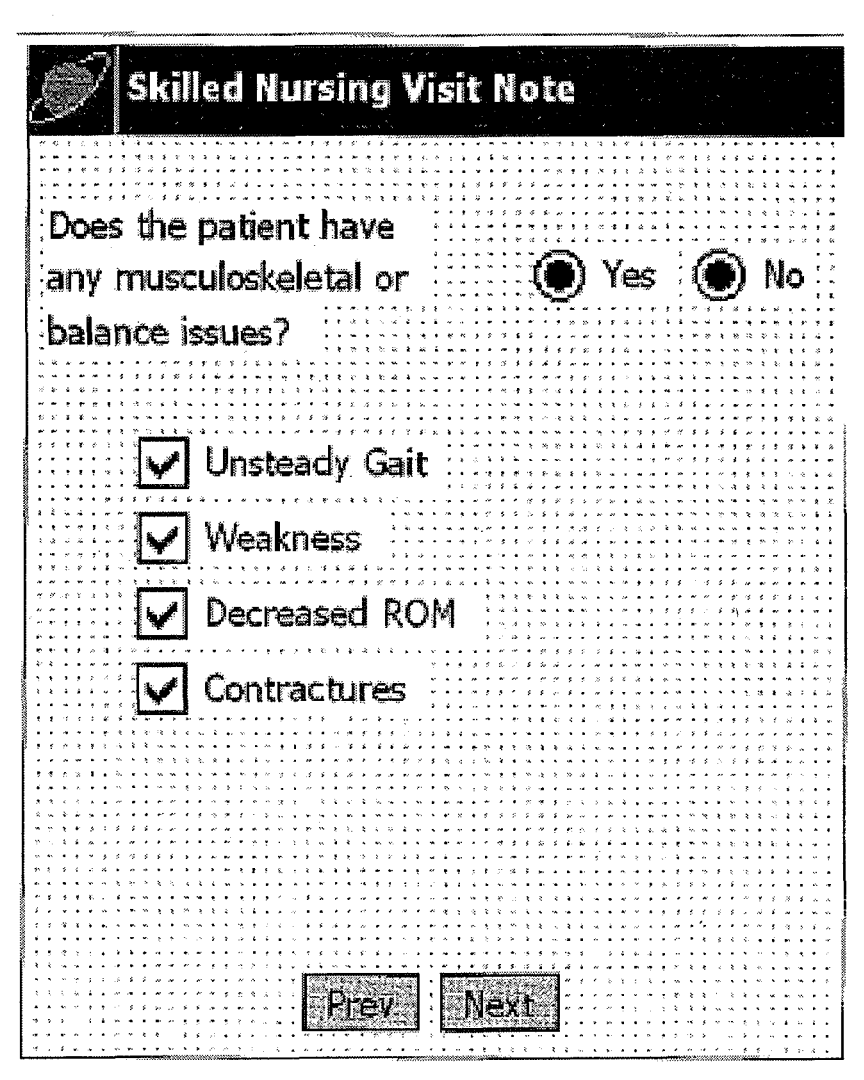

FIG. 26 shows an example of a user interface screen for allowing a caregiver to input information as to whether the patient has any musculoskeletal or balance issues. For example, the caregiver can specify whether the patient has an unsteady gait, weakness, decreased range of motion (ROM), or contractures.

Figure 27:

FIG. 27 shows an example of a user interface screen for allowing a caregiver to specify whether the patient has any neurosensory problems or deficits. For example, the caregiver can specify whether the patient has syncope, headaches, tremors, vertigo, decreased sensitivity, speech impairment, hearing impairment, vision impairment, swallowing difficulties, etc.

Figure 28:

FIG. 28 shows an example of a user interface screen for allowing a caregiver to input information as to the patient's emotional status and whether it is within normal limits. For example, the caregiver can identify whether the patient is disoriented, depressed, forgetful, angry withdrawn, etc.

Figure 29:
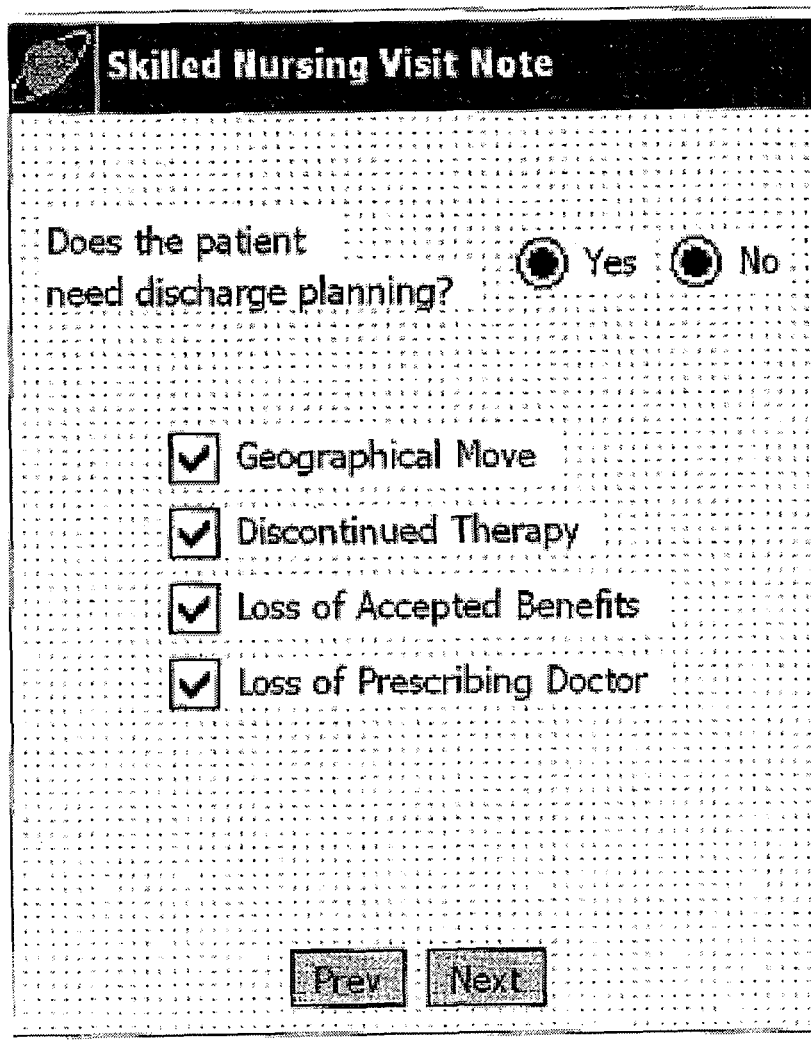

FIG. 29 shows an example of a user interface screen for allowing a caregiver to input information as to whether the patient requires discharge planning. The caregiver can specify whether a geographical move is required, if therapy should be discontinued, if there is a loss of accepted benefits, or if there is a loss of the patient's prescribing doctor.

Figure 30:

FIG. 30 shows an example of a user interface screen for allowing a caregiver to enter information regarding special interventions that may be required for the patient, and instructions relating thereto. For example, the caregiver could specify whether a skilled assessment is required, whether observation for infection is required, whether teaching is required relating to physiology or disease, whether observation of the patient's activities of daily living (ADL) are required, whether a review is required of safety factors, whether review of the patient's medication and/or teaching is required, or other assessment.

Figure 31:

FIG. 31 shows an example of a user, interface screen for allowing a caregiver to enter progress notes and to date and electronically sign a report. The caregiver's signature can be entered using a stylus (such that the caregiver physically signs his/her signature on the screen of the smart phone using the stylus), and captured as a digital file. The system could be programmed so that a caregiver's report is only valid if a signature is obtained from the caregiver. Moreover, the system could be programmed so that the caregiver cannot complete a report unless and until a signature is entered. The progress notes could include information and/or alerts about the progress of a patient's treatment, and they could be transmitted electronically (e.g., via e-mail) to a medical professional (e.g., to a doctor) so that the medical professional can monitor the progress and effectiveness of treatment. Further, such notes could assist a medical professional with disease state management for a patient, allowing the medical professional to be proactive in treating the patient and to decide next steps for treating the patient utilizing the information and/or alerts provided by the progress notes.

Figure 32:

FIG. 32 shows an example of a user interface screen for allowing a caregiver to enter information nutritional status information about a patient. For example, the caregiver can identify whether the patient is experiencing heartburn or a change in weight, as well as the patient's current diet and appetite.

Figure 33:
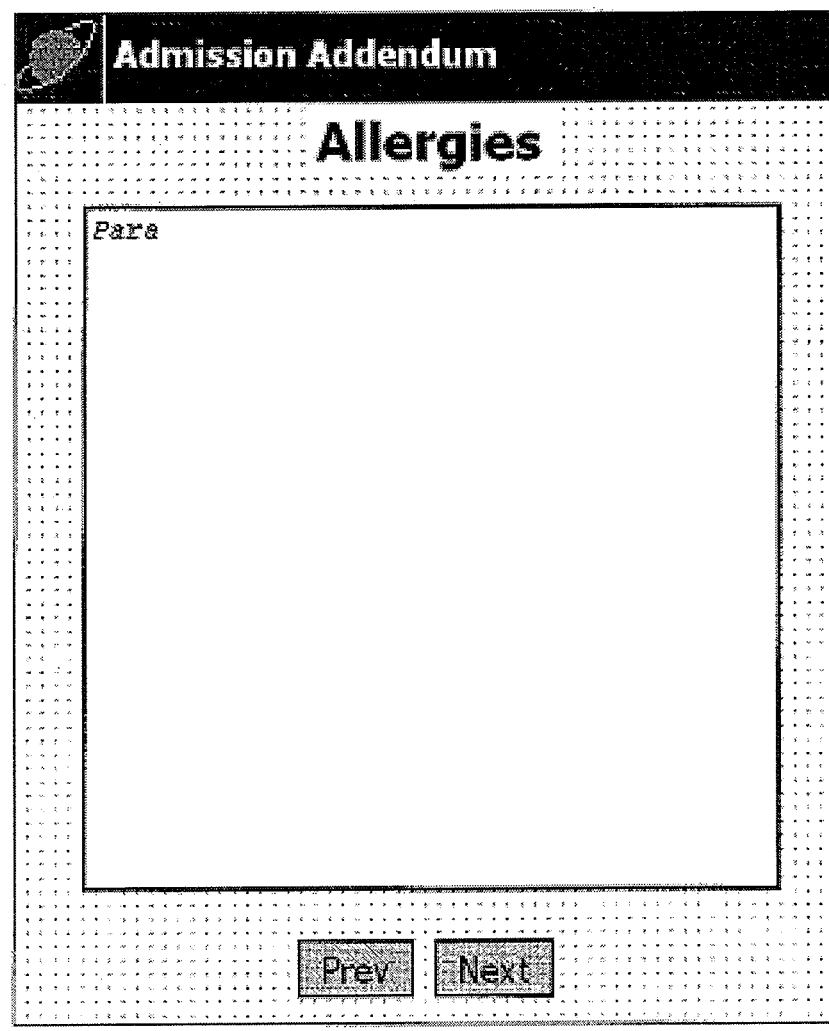

FIG. 33 shows an example of a user interface screen for allowing a caregiver to enter information about any allergies that the patient may be experiencing.

Figure 34:

FIG. 34 shows an example of a user interface screen for allowing a caregiver to enter information about the patient's eyes and/or ears, such as whether the patient wears glasses, has glaucoma, is legally blind, has blurred vision, is hard of hearing (HoH), has tinnitus, is experiencing vertigo, or is deaf.

Figure 35:
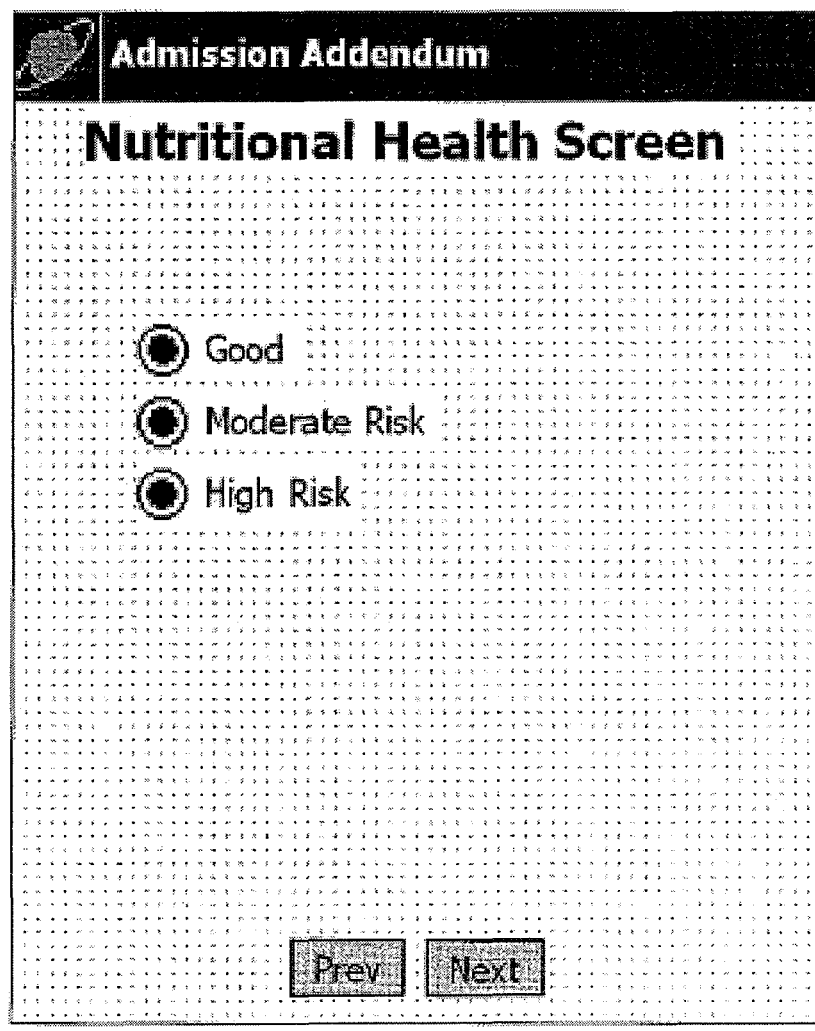

FIG. 35 shows an example of a user interface screen for allowing a caregiver to enter information about the patient's nutritional health. The caregiver can indicate whether the patient's nutritional health is good, or if there is a moderate or high risk of malnutrition.

Figure 36:

FIG. 36 shows an example of a user interface screen for allowing a caregiver to enter information about medical equipment that the patient is using. For example, the caregiver can identify whether the patient is using a cane, a walker, a wheelchair, a hospital bed, or a shower chair.

Figure 37:
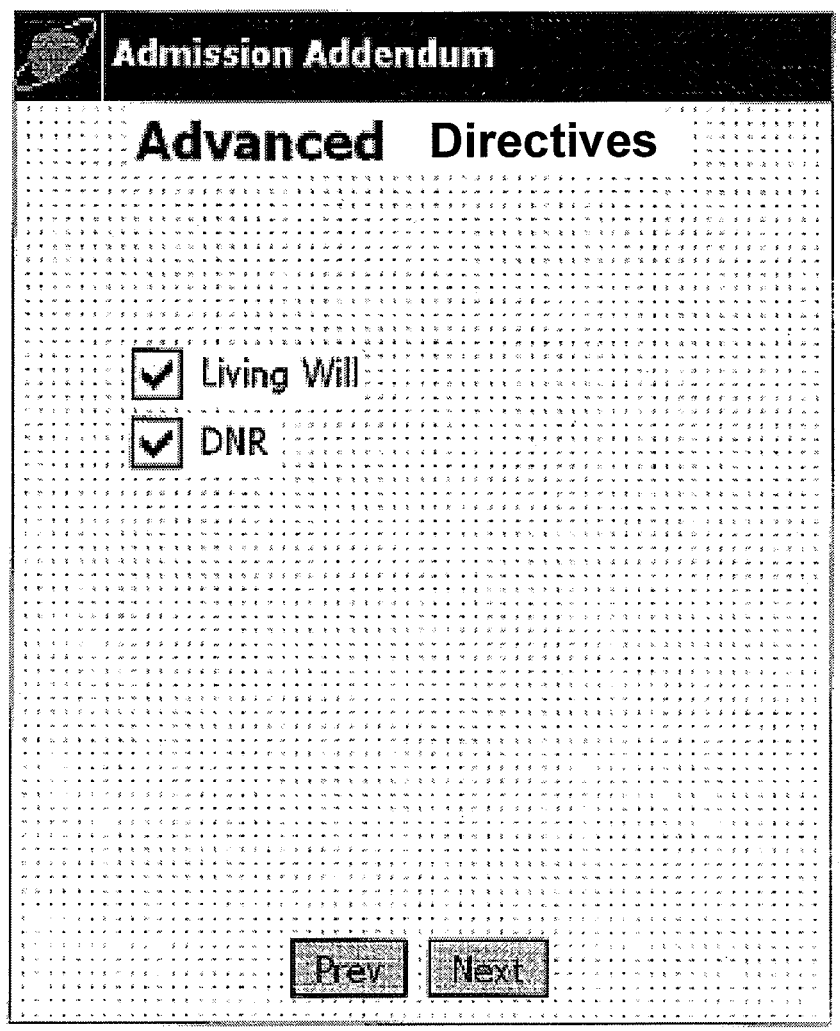

FIG. 37 shows an example of a user interface screen for allowing a caregiver to indicate whether the patient has any advanced directives, such as a living will or a do not resuscitate (DNR) order.

Figure 38:

FIG. 38 shows an example of a user interface screen for allowing a caregiver to input information about the patient's living arrangement, e.g., whether the patient lives in a house, in an apartment, in an assisted care facility (ACF), alone, or with others.

Figure 39:

FIG. 39 shows an example of a user interface screen for allowing a caregiver to input information about whether the patient is experiencing any functional limitations. For example, the caregiver can record whether the patient is experiencing shortness of breath (SOB) with exertion, increased bowel or bladder output, paralysis, endurance, or ambulation.

Figure 40:
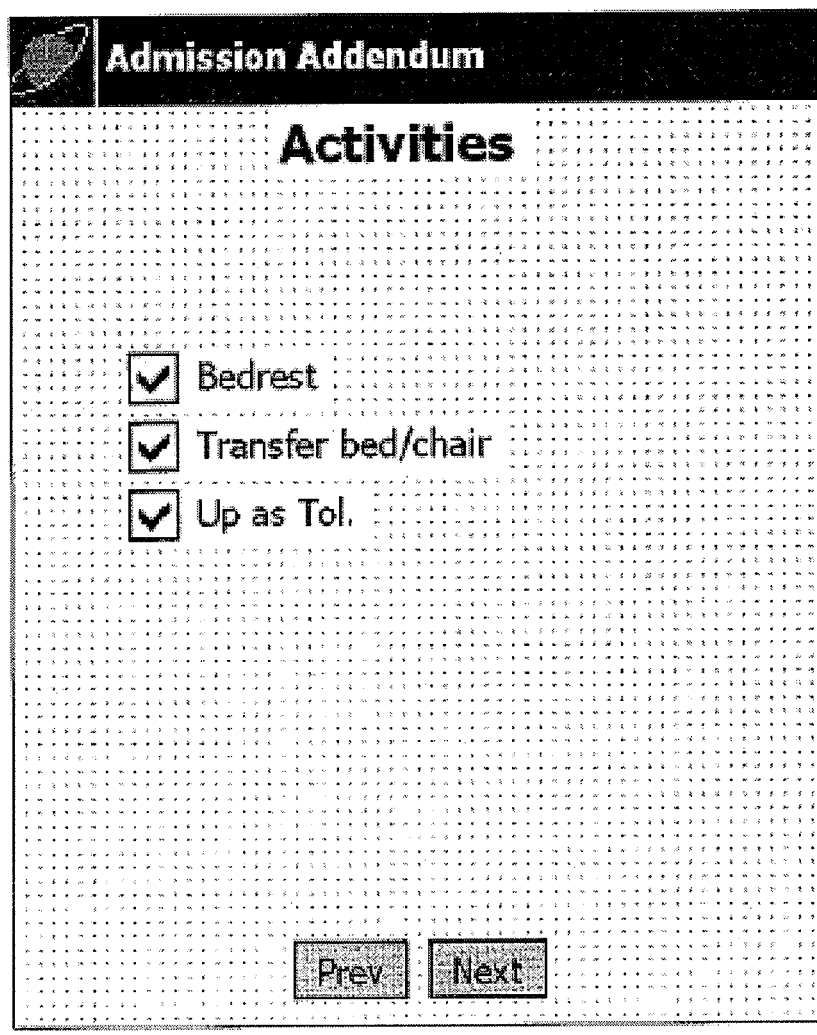

FIG. 40 shows an example of a user interface screen for allowing a caregiver to input information about activities that the patient may engage in, such as bedrest, transfer to/from a bed or chair, or standing up (as tolerated by the patient).

Figure 41:

FIG. 41 shows an example of a user interface screen for allowing a caregiver to input information about safety measures relating to a patient. For example, the caregiver can identify whether any precautions should be taken in connection an oxygen supply for the patient, whether pathways should be cleared for the patient, whether to lock a bathroom (water closet) upon transfers of the patient, whether any infection control measures should be taken, whether an emergency preparedness plan was discussed, and whether any medical backup procedures were discussed.

Figure 42:

FIG. 42 shows an example of a user interface screen for allowing a caregiver to enter information relating to assisted daily living, such as whether the patient is eating, whether the patient requires a transfer to another facility, whether there are any issues relating to pressing, grooming, bathing, and/or toileting, whether the patient has any ambulation problems, whether the patient's medications must be managed, and whether the patient requires assistance with communication, meal preparation, housekeeping, telephone usage, reading, and/or writing.

Figure 43:
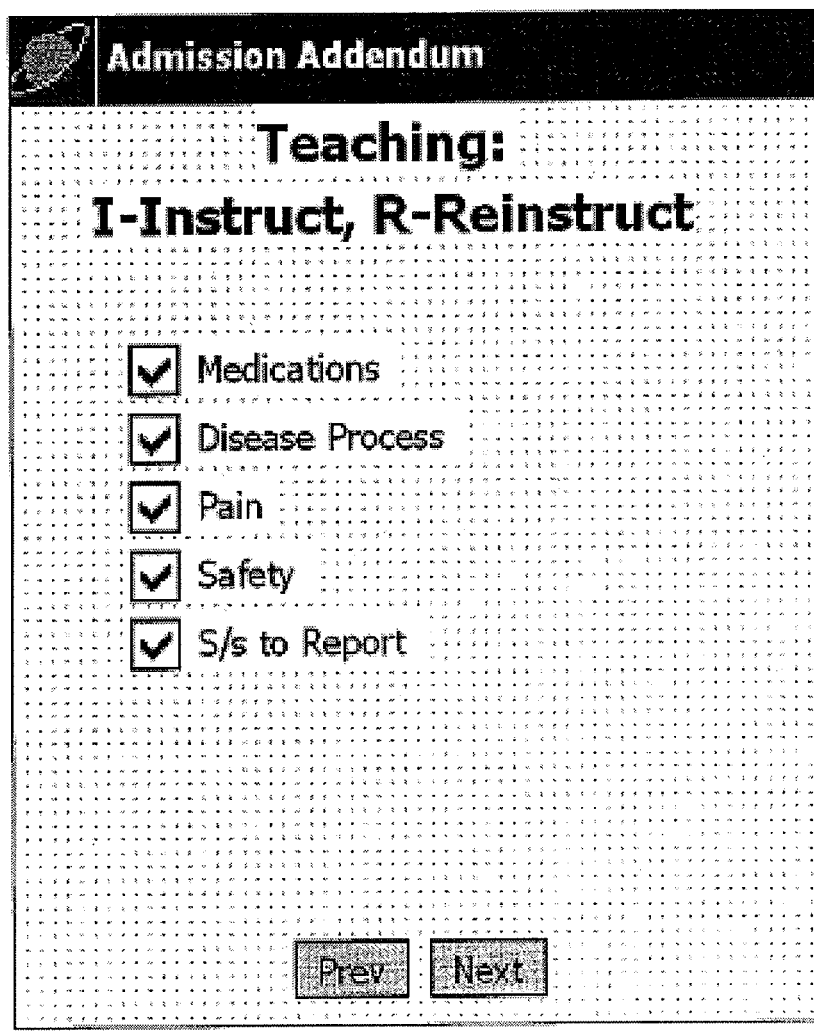

FIG. 43 shows an example of a user interface screen for allowing a caregiver to input information relating to teaching requirements for a patient. For example, the caregiver can identify whether the patient requires instruction (or reinstruction) regarding the usage of medications, disease process, pain, safety, and/or other issues to report.

Figure 44:
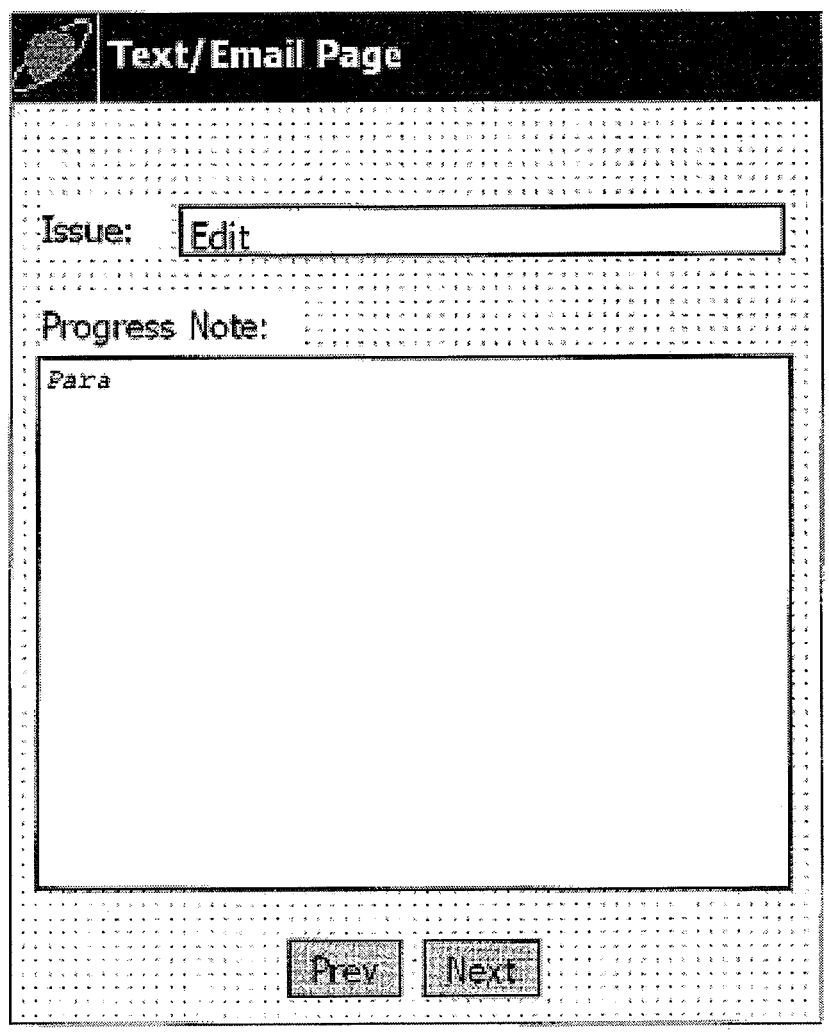

FIG. 44 shows an example of a user interface screen for allowing a caregiver to create a text or e-mail to be sent to a recipient, such as the caregiver's supervisor, a medical professional (e.g., doctor, nurse), etc. This allows the caregiver to remotely communicate with supervisors/medical professionals while the caregiver is at the patient's location, thereby allowing for rapid consultations with other individuals if and when such consultations may be necessary or desirable.

Figure 45:

FIG. 45 shows an example of a user interface screen for allowing a caregiver to capture telemetry information relating to an in-home medical device operated by a patient. For example, the caregiver can identify whether a personal therapy management (PTM) device is enabled, whether any changes were found in the device since the caregiver's last visit, and whether any changes should be implemented (such as a new dosage, new duration for a dosage, new lock-out time interval, and maximum number of activations permitted per day.

Figure 46:
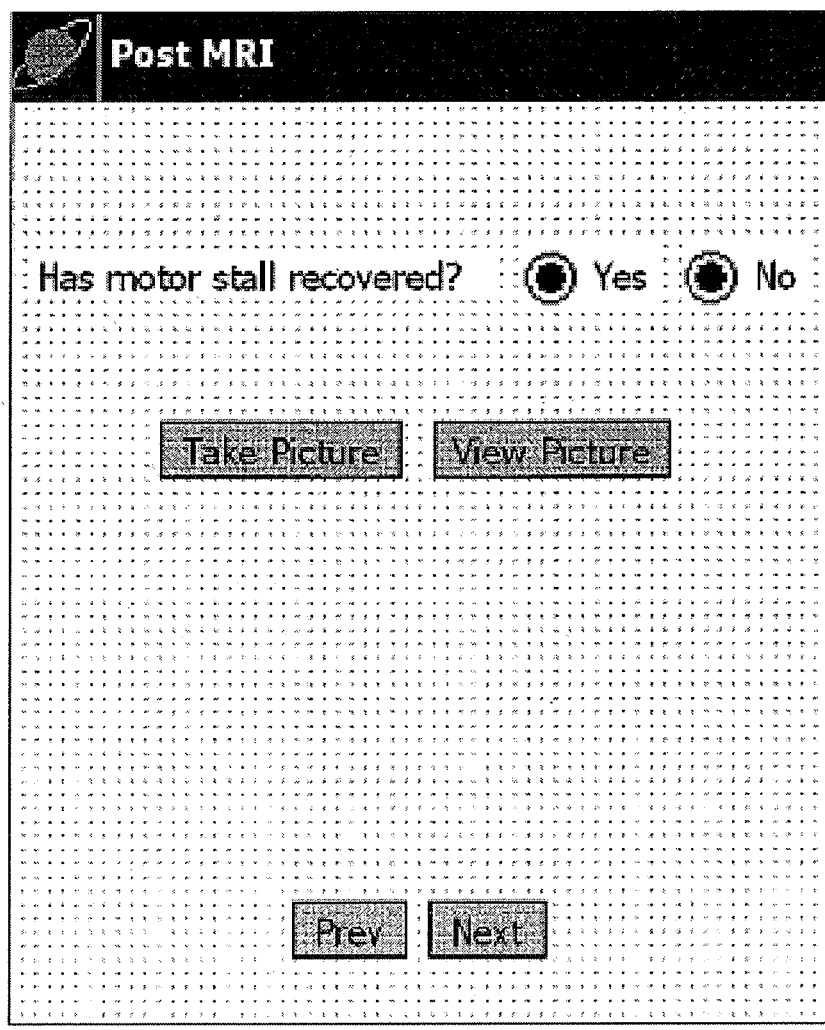

FIG. 46 shows an example of a user interface screen for allowing a caregiver to identify whether there are any problems associated with an in-home medical device, such as whether a motor stall (in an in-home infusion pump) has been recovered. Also, this screen permits the caregive to take a picture of the device, if desired.

Figure 47:

FIG. 47 shows an example of a user interface screen for allowing a caregiver to record additional information relating to an in-home medical device. For example, if the in-home medical device is an infusion pump, the caregiver can identify whether the operation mode is simple continuous, flex, or complex continuous. Moreover, the caregiver can identify whether the manufacturer's recommended kit is being used with the pump, and if not, a reason can be provided.

Figure 48:

FIG. 48 shows an example of a user interface screen for allowing a caregiver to enter information about syringes and labels associated therewith. The caregiver can identify whether there is a syringe label to identify, and whether the syringe label matches the current orders and/or infusion pump settings.

Figure 49:
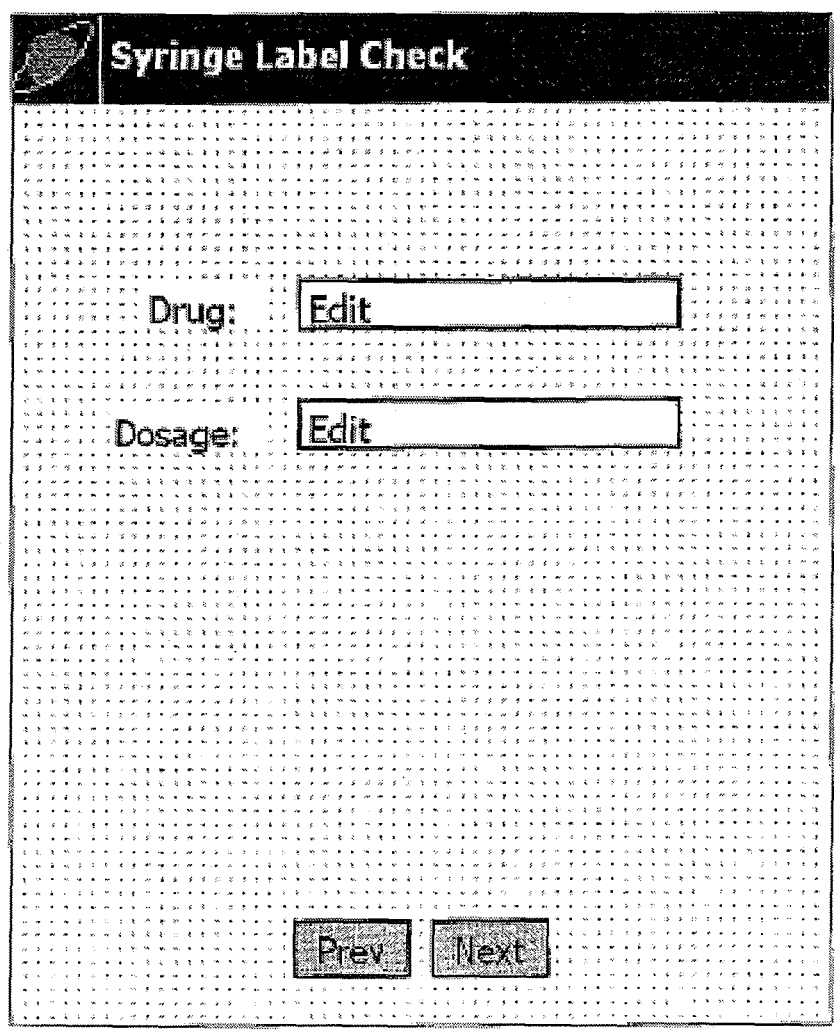

FIG. 49 shows an example of a user interface screen for allowing a caregiver to enter information about a drug to be delivered to a patient, and the dosage for the drug. As mentioned above, the information provided can be compared to pre-defined thresholds to determine whether the appropriate drug and/or dosage is about to be delivered to the patient. If either of these parameters are not acceptable, the system can display a screen requiring the caregiver to take corrective action, or the system can be locked and a screen displayed requiring the caregiver to place a telephone call to a supervisor. The system thus assists with preventing improper drugs and/or dosages from being given to a patient.

Figure 50:
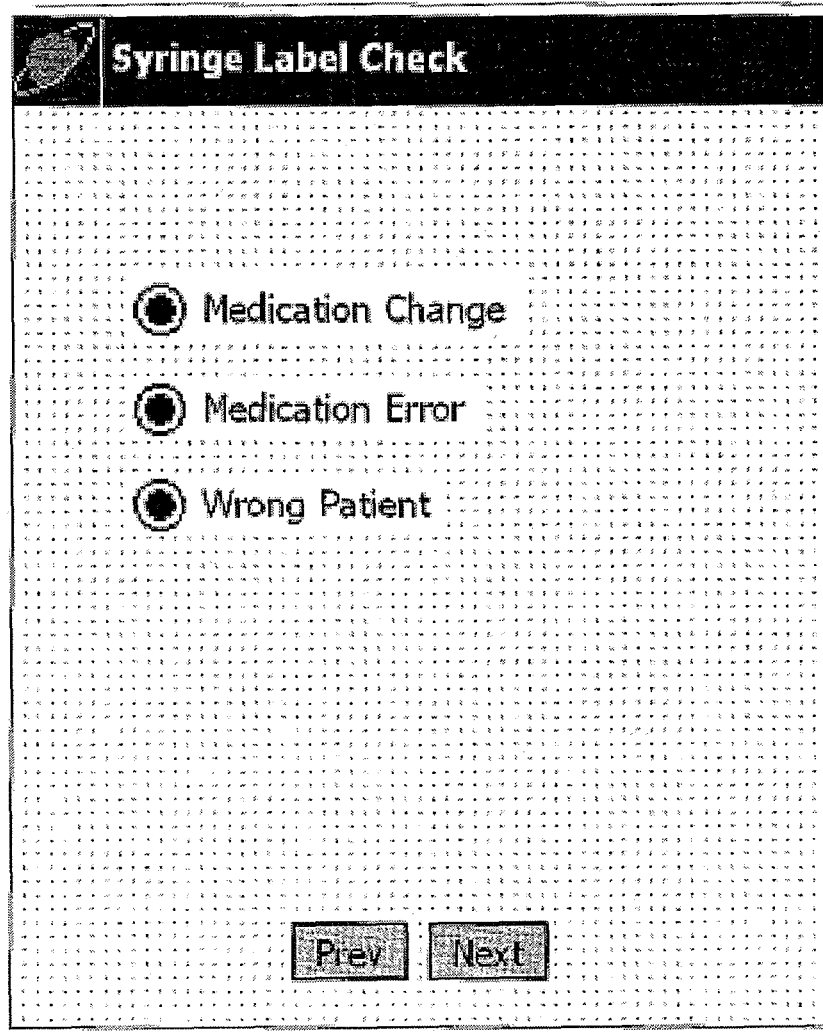

FIG. 50 shows an example of a user interface screen for allowing a caregiver to input additional information relating to medications to be given to a patient. For example, the caregiver can identify whether a medication change has occurred, whether the wrong medication has been prescribed, or whether the medication is for the wrong patient.

Figure 51:
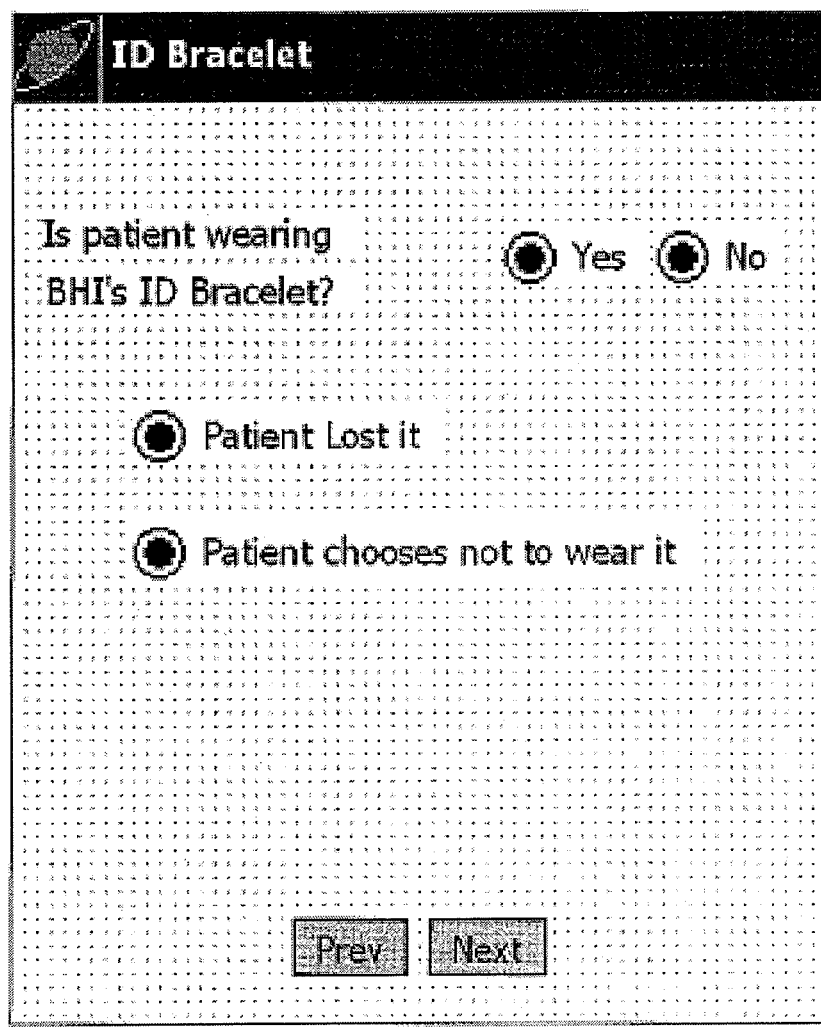

FIG. 51 shows an example of a user interface screen for allowing a caregiver to input information relating to a patient's identification bracelet. The caregiver can identify whether an identification bracelet is being worn by the patient, whether the patient lost it, or whether the patient chooses not to wear it.

Figure 52:
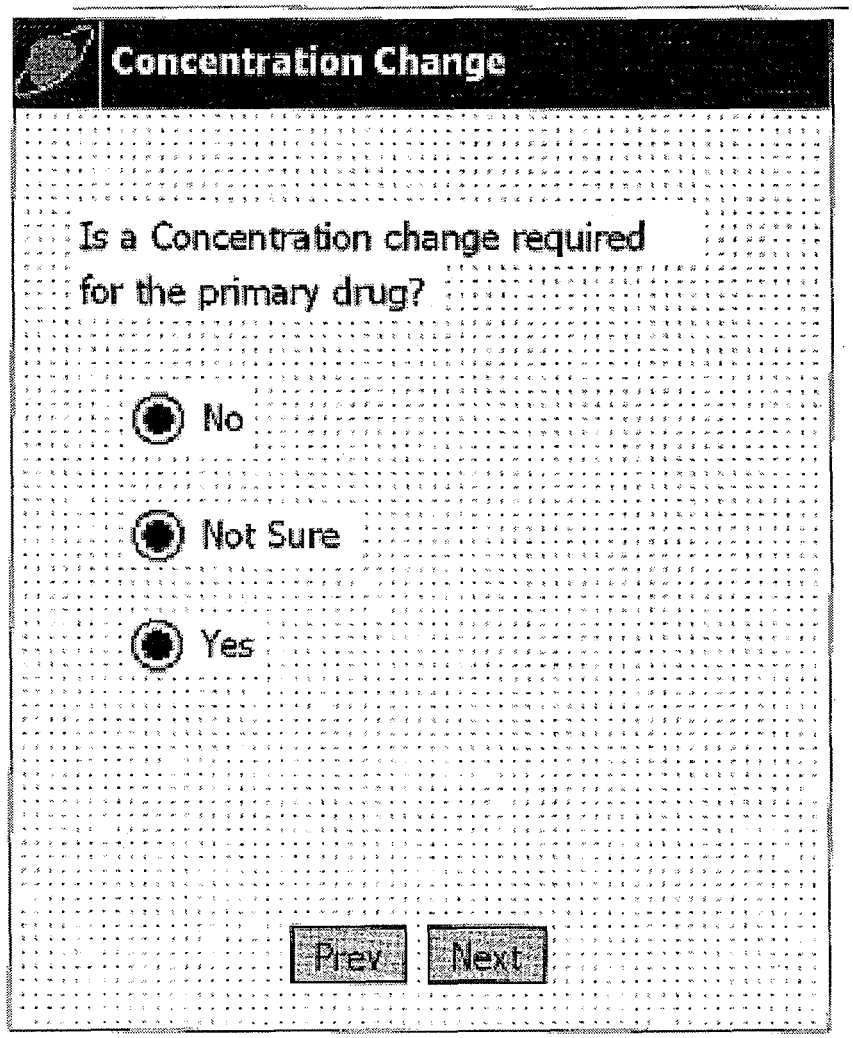

FIGS. 52-53 show examples of user interface screen for allowing a caregiver to indicate whether a concentration change is required for a primary drug to be delivered to a patient (FIG. 52), and to provide detailed information about such changes (FIG. 53). The caregiver can specify changes in concentration (e.g., expressed in milliliters (ml)), whether a reservoir rinse is required, quantity of preservative-free normal saline used to perform reservoir rinse, and quantity of new medication wasted during the rinse.

Figure 54:
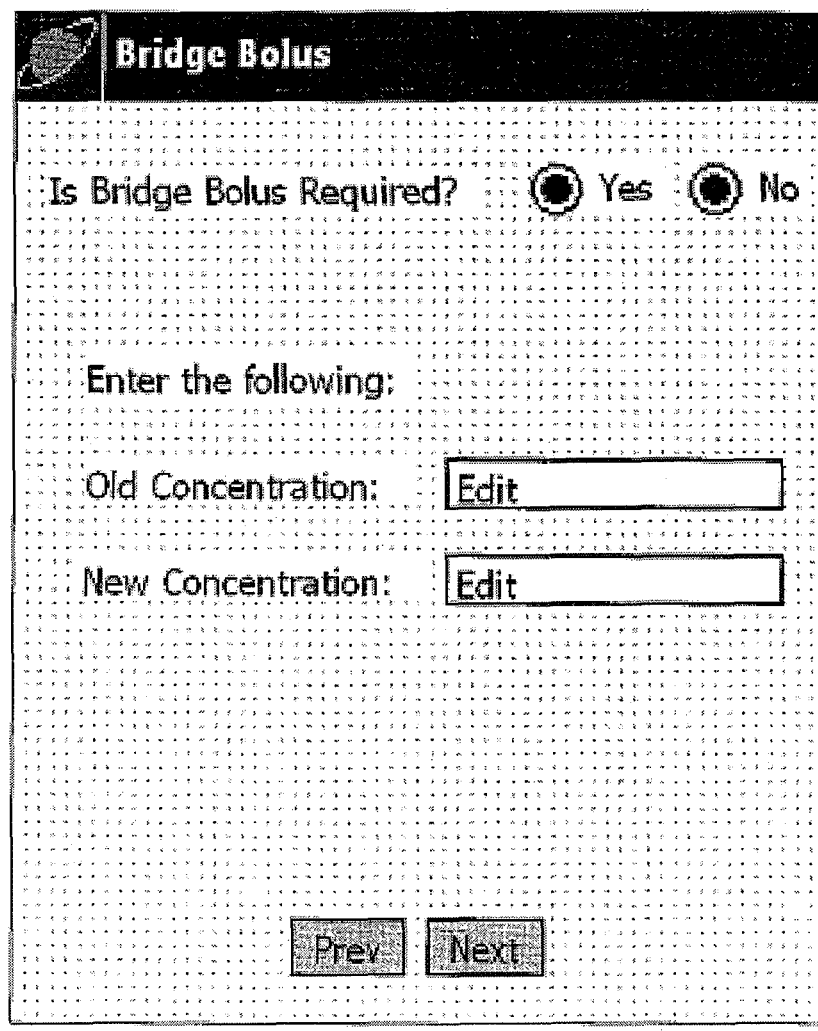

FIG. 54 shows an example of a user interface screen for allowing a caregiver to enter information about a bridge bolus for the patient. The caregiver can identify whether a bridge bolus is required, and can provide information about the bolus, such as old concentration and new concentration levels.

Figure 55:
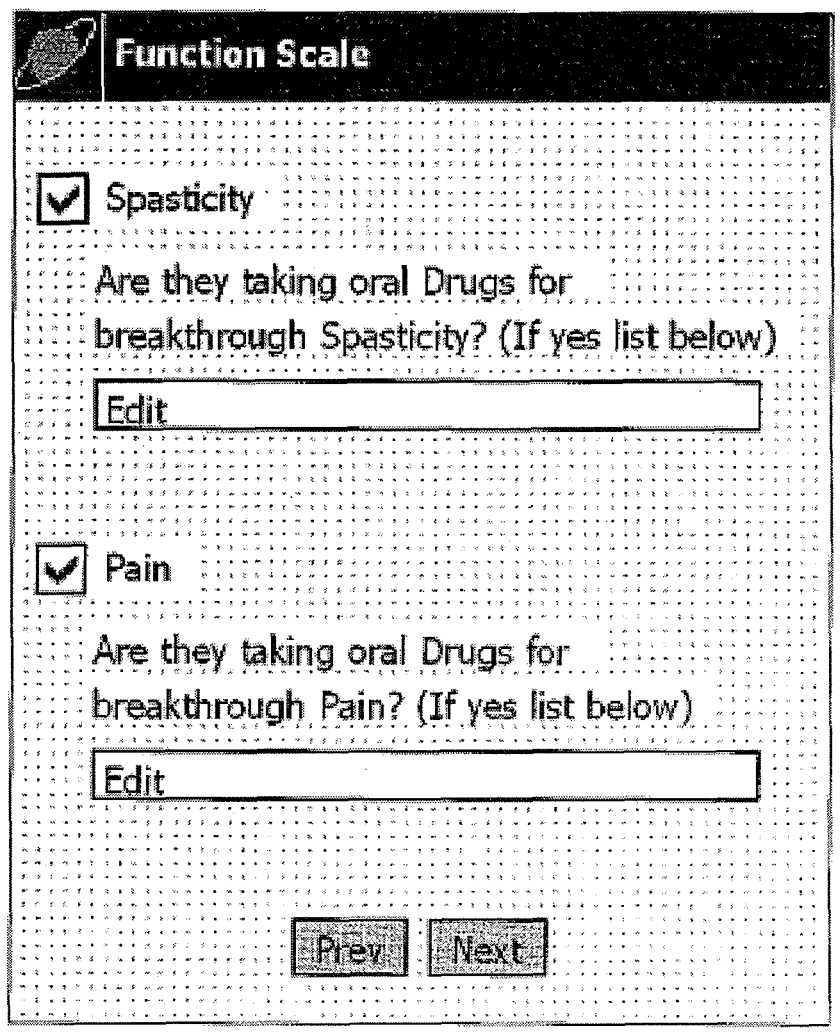

FIG. 55 shows an example of a user interface screen for allowing a caregiver to input information relating to the patient's function. A caregiver can enter information relating to spasticity and pain, and identify any drugs that the patient may be taken to alleviate spasticity and pain.

Figure 56:
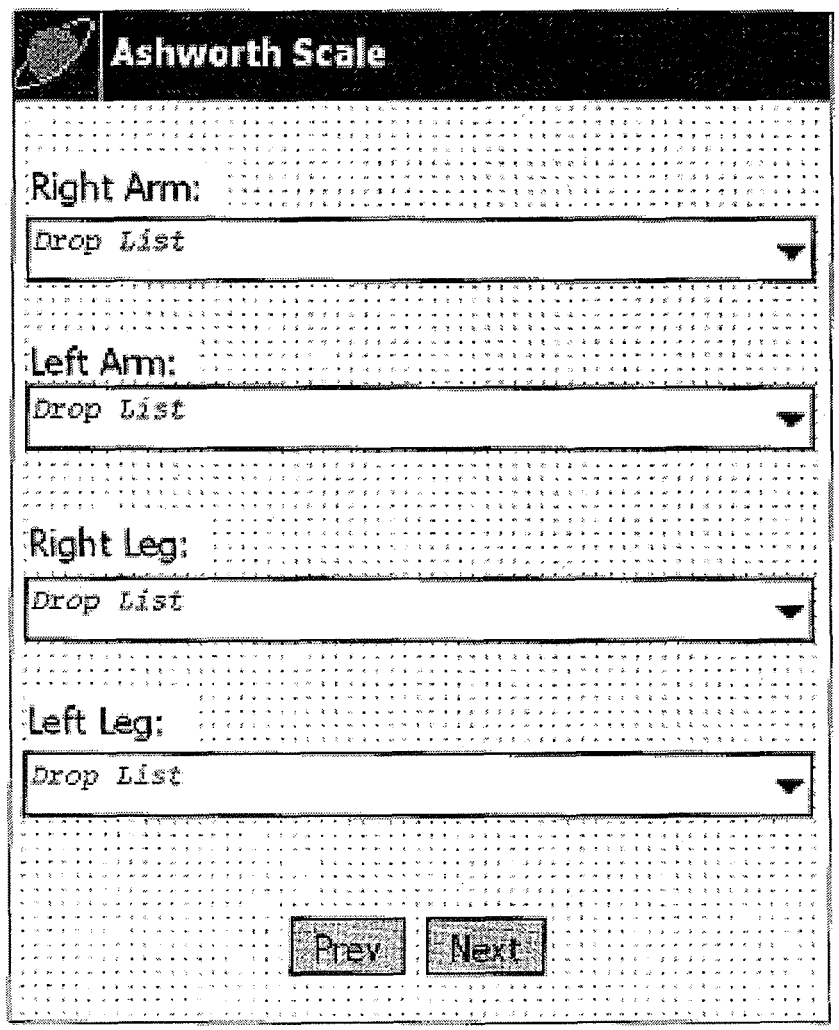

FIG. 56 shows an example of a user interface screen for allowing a caregiver to indicate a patient's spasticity levels for arms and legs using an Ashworth scale. The caregiver can identify scale values for each arm and leg by clicking on a pull-down list for each arm or leg and selecting the appropriate value.

Figure 57:
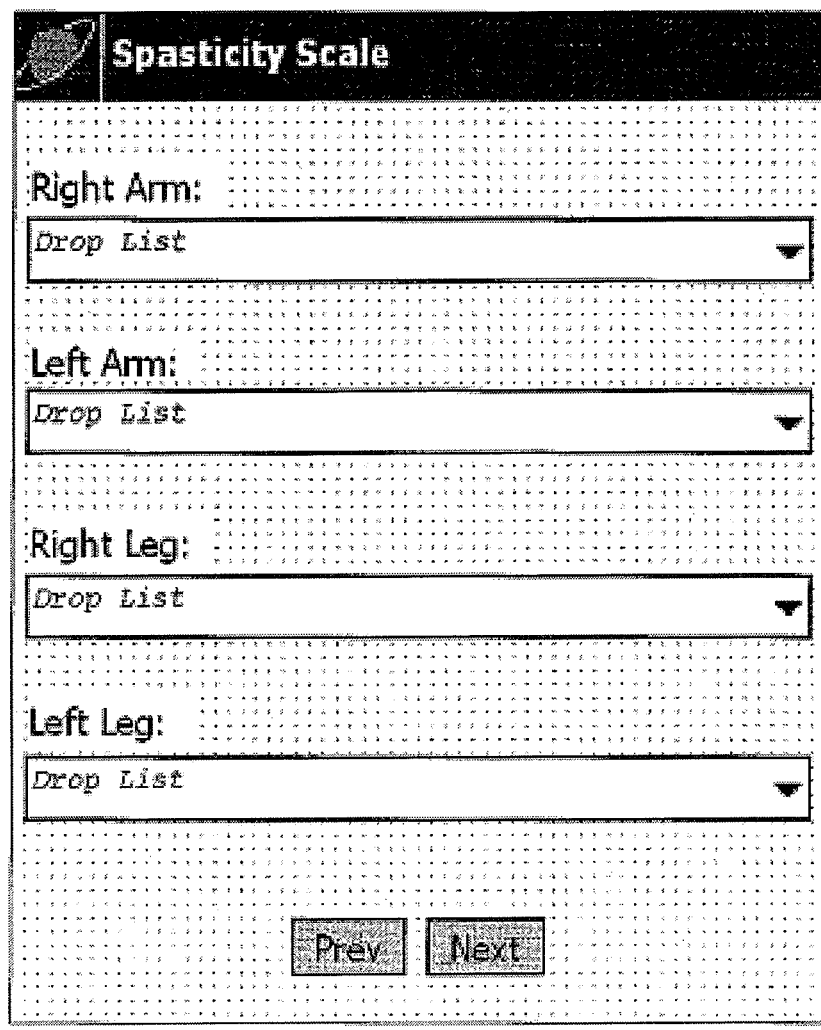

FIG. 57 shows an example of a user interface screen for allowing a caregiver to indicate a patient's spasticity levels for arms and legs using a spasticity scale. The caregiver can identify scale values for each arm and leg by clicking on a pull-down list for each arm or leg and selecting the appropriate value.

Figure 58:

FIG. 58 shows an example of a user interface screen for allowing a caregiver to record detailed information about pain a patient may be experiencing. A caregiver can record information about the origin of the patient's pain, location of the pain, quality of the pain, intensity level, and duration.

Figure 59:

FIG. 59 shows an example of a user interface screen for allowing a caregiver to input information relating to an implanted infusion pump being used by a patient. The caregiver can identify whether the patient's skin near the pump site is intact, and can take and/or view a picture of the pump site. Also, the caregiver can identify whether the implant has been in place less than a predefined period of time (e.g., two weeks), whether it appears to be normal, and whether there are any other adverse indications by the patient such as seroma, swelling, tenderness, redness, drainage, and warmth.

Figure 60:
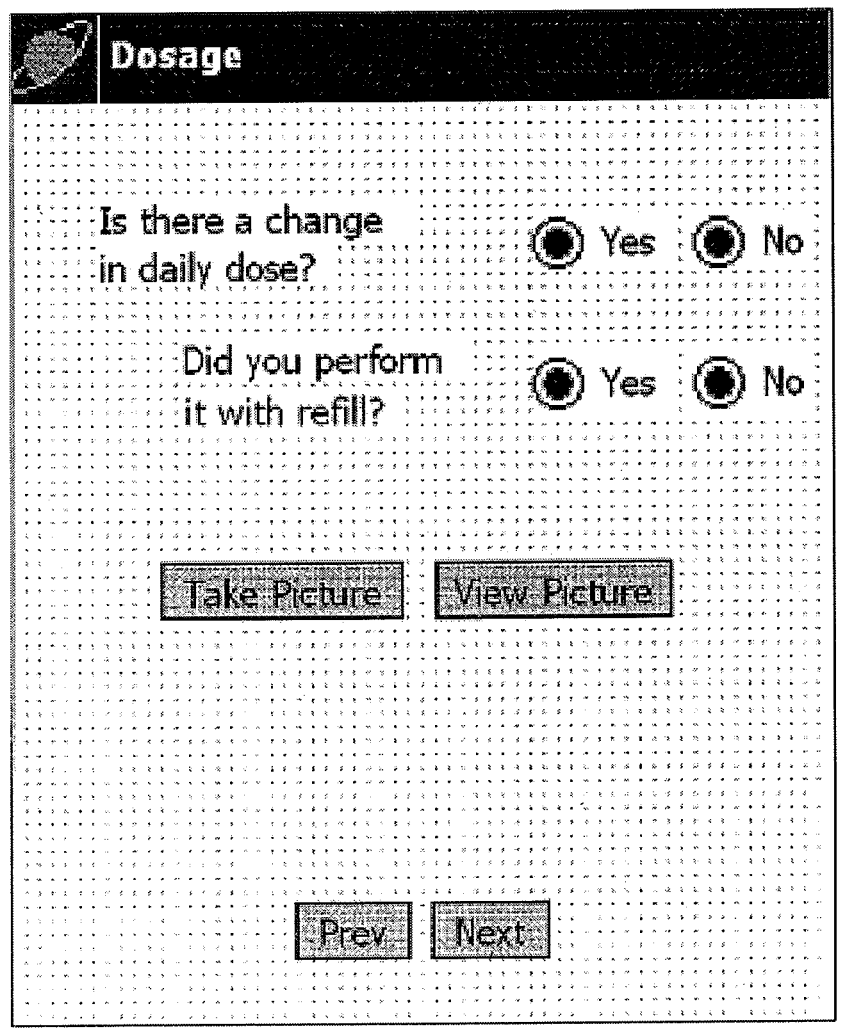

FIG. 60 shows an example of a user interface screen for allowing a caregiver to input information relating to changes in dosages for the patient. The caregiver can identify whether there has been a change in the patient's daily dose, and whether the change in dosage was performed with a refill. Also, the caregiver can take and/or view a picture of the dose.

Figure 61:
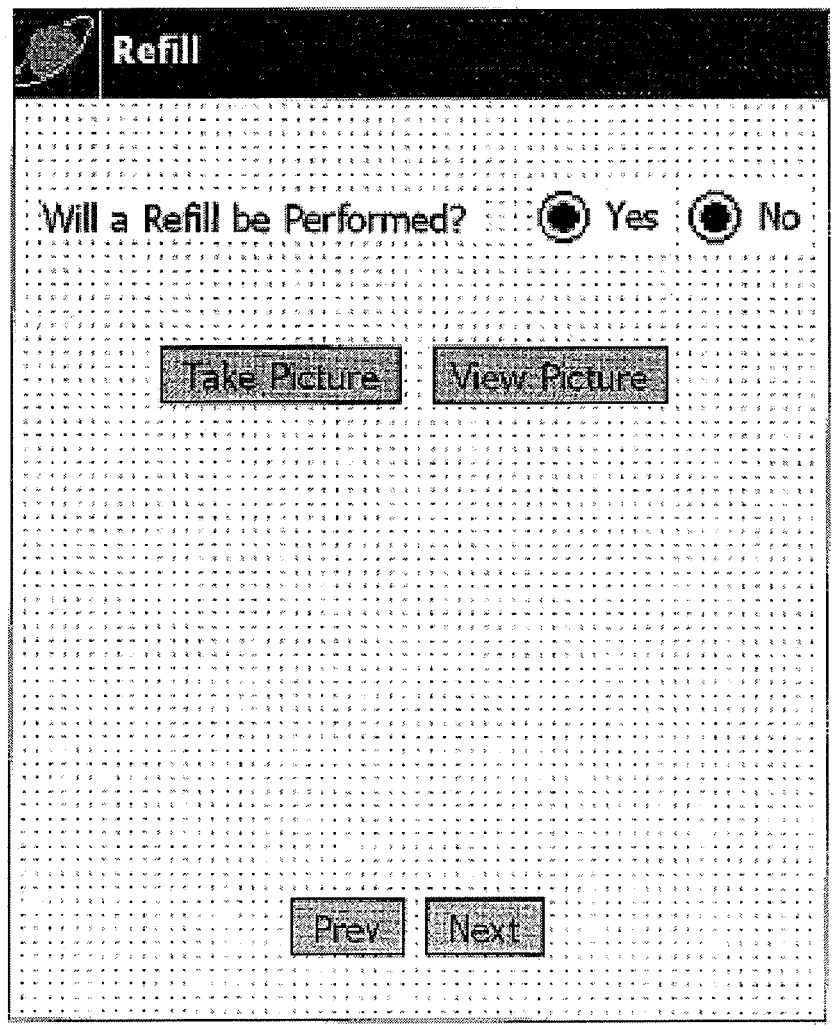

FIG. 61 shows an example of a user interface screen for allowing a caregiver to provide information relating to drug refills. In this screen, the caregiver can identify whether a refill will be performed, and can take and/or view a picture of a prescription to be refilled.

FIG. 62 shows an example of a user interface screen for allowing a caregiver to provide additional information relating to drug refills. The caregiver can identify a plurality of drugs, as well as current doses for each drug and new doses (expressed, e.g., in ml).

Figure 63:
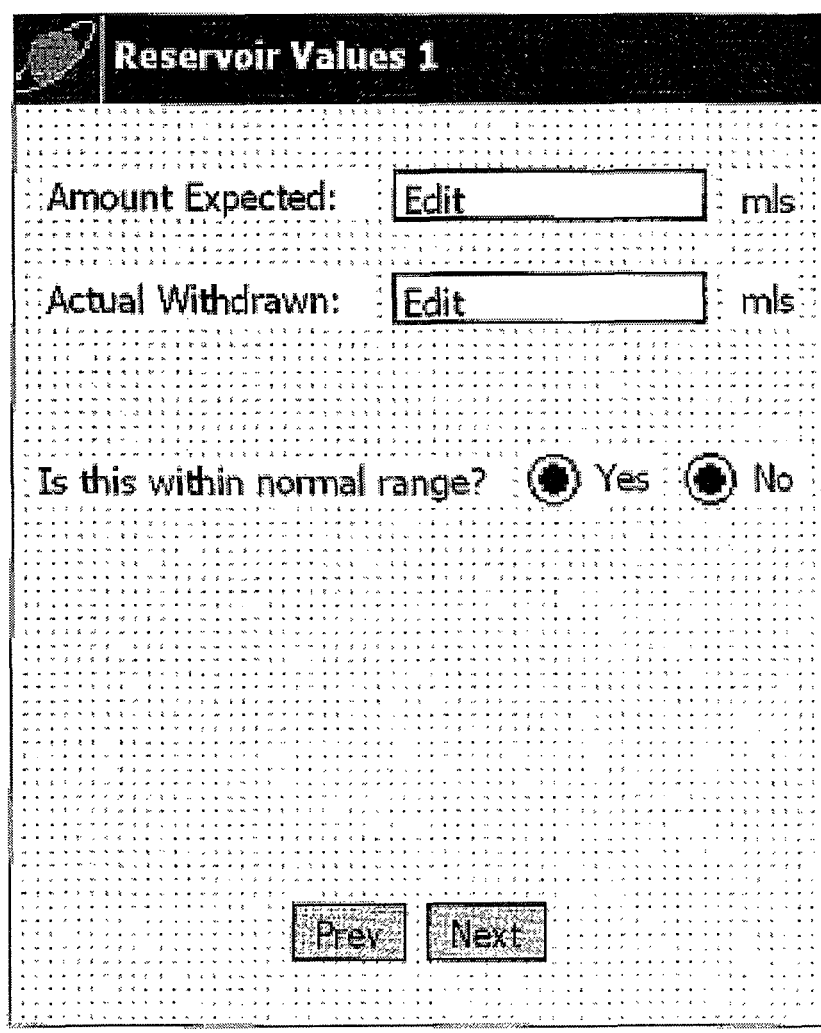

FIG. 63 shows an example of a user interface screen for allowing a caregiver to input information relating to reservoirs used in connection with drug doses. In this screen, the caregiver can identify an amount of fluid expected from the reservoir, the actual amount withdrawn, and whether the amount withdrawn is within a normal range.

Figure 64:

FIG. 64 shows an example of a user interface screen for allowing a caregiver to record information relating to changes in daily drug doses for a patient. In this screen, a caregiver an identify one or more drugs being taken by the patient, as well as the current daily dosage for the drug and a new daily dosage for the drug.

Figure 65:
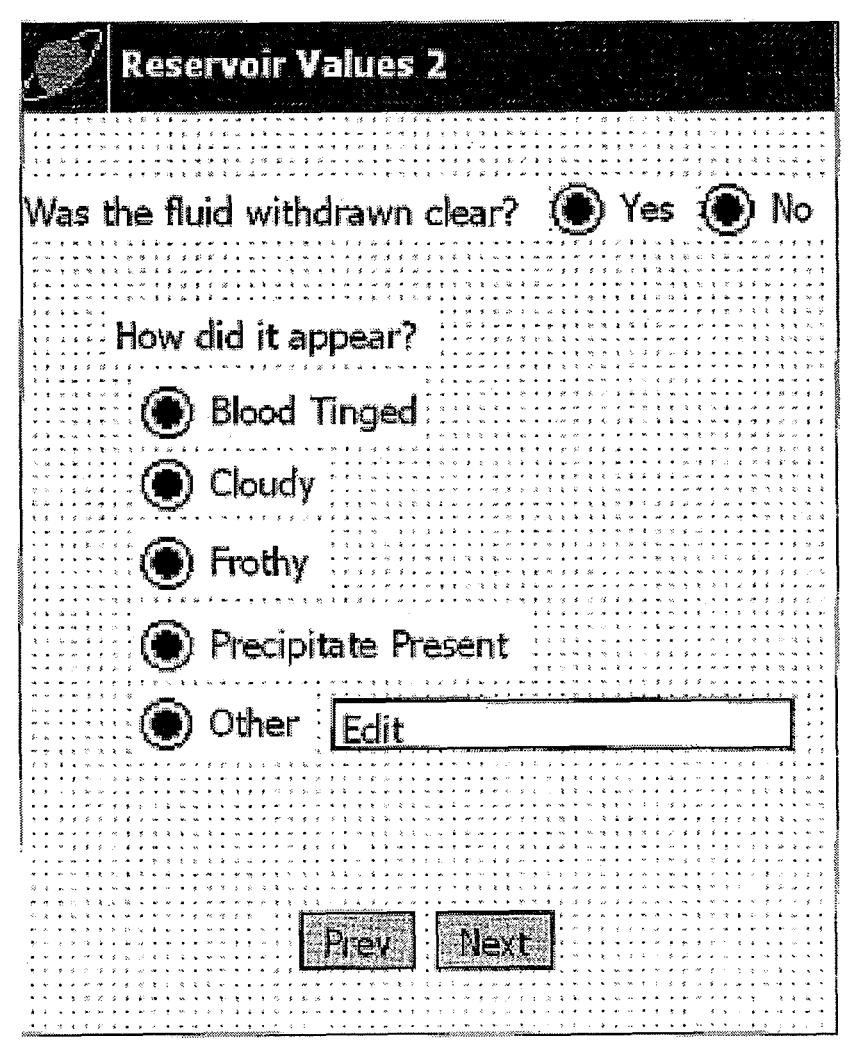

FIG. 65 shows an example of a user interface screen for allowing a caregiver to record information relating to fluid drawn from a reservoir, such as whether any fluid was drawn by the caregiver, and if so, its appearance.

Figure 66:

FIG. 66 shows an example of a user interface screen for allowing a caregiver to input information relating to syringes used to treat a patient. In this screen, the caregiver can input information relating to syringe volume, quantity dispensed, quantity wasted to prime filter (of an implanted infusion pump), volume instilled into pump, discard volume, etc. Also, the screen allows for calculation of the appropriate discarded volume, and an electronic signature of the caregiver.

Figure 67:
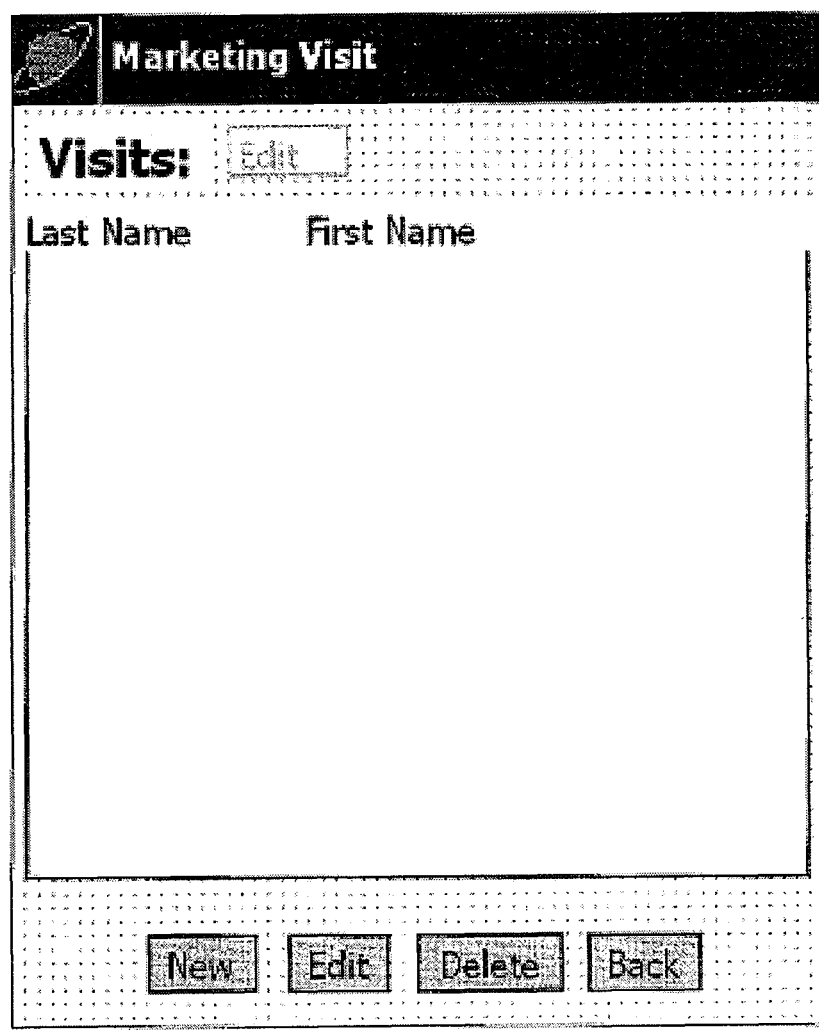

FIG. 67 shows an example of a user interface screen for allowing a caregiver to store and/or edit information about marketing visits made to various locations, including the identities of individuals with whom the caregiver has met.

Figure 68:
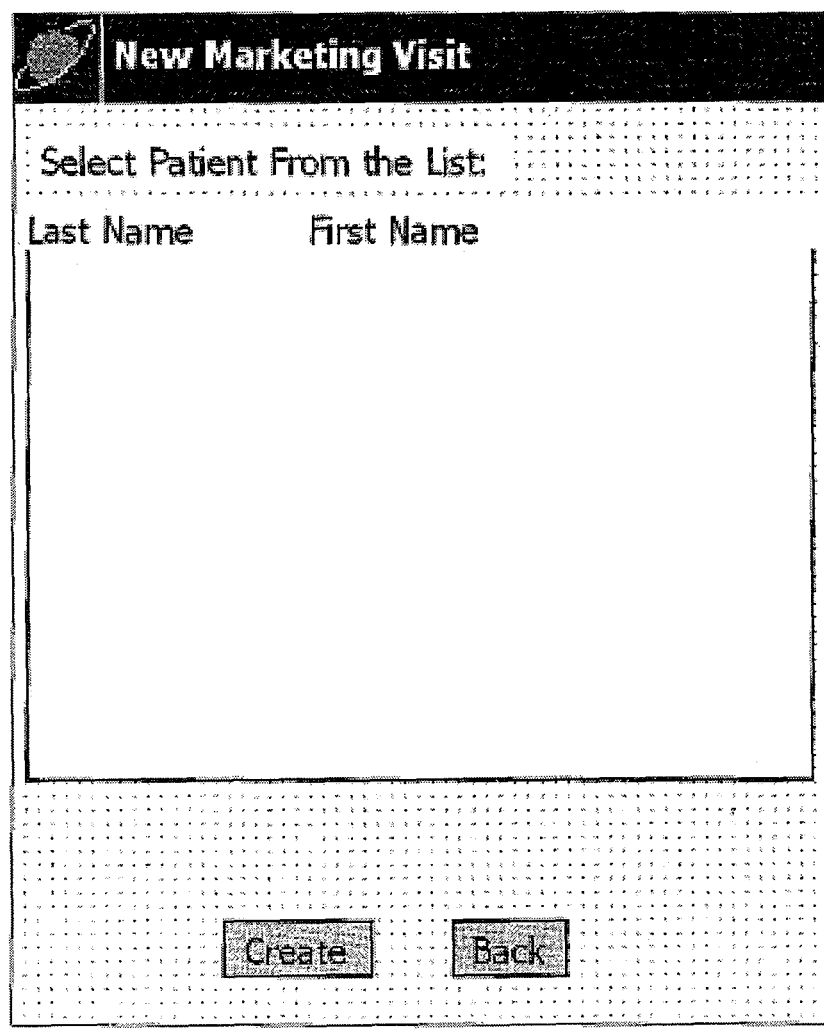

FIG. 68 shows an example of a user interface screen for allowing a caregiver to select/identify patients for new marketing visits. Patients can be selected by clicking on a list of patients in the screen.

Figure 69:
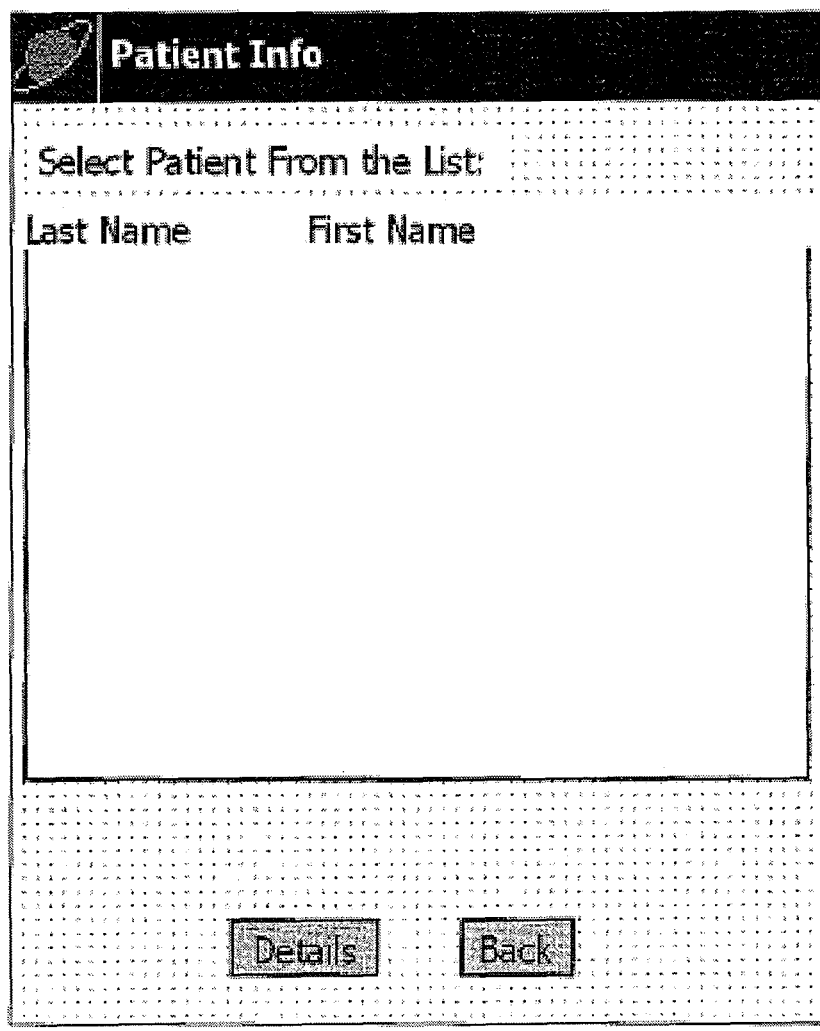

FIG. 69 shows an example of a user interface screen for allowing a caregiver to select a patient from a list of patients, for subsequent entry of information about the patient.

FIG. 70 shows an example of a user interface screen for allowing a caregiver to add or update physician information. In this screen, the caregiver can input a doctor name, address, and contact information.

Figure 71:
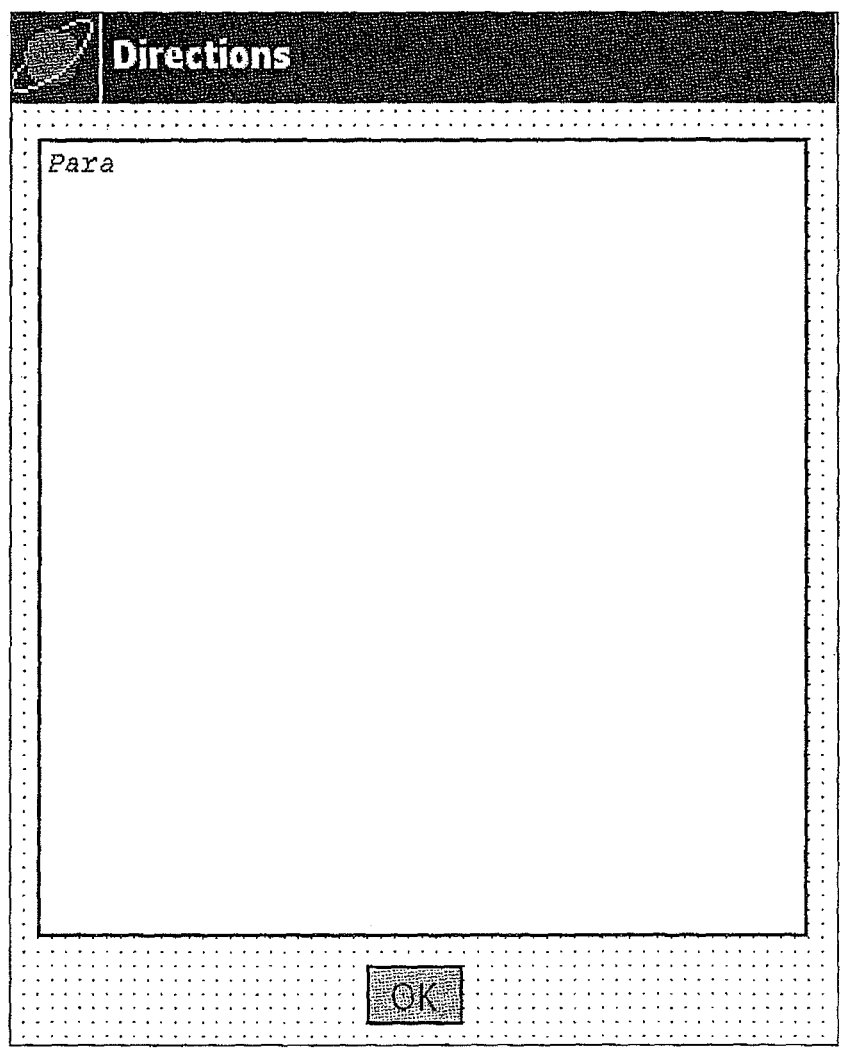

FIG. 71 shows an example of a user interface screen for allowing a caregiver to record specific directions relating to care of a patient, for later use by a medical professional.

Figure 72:
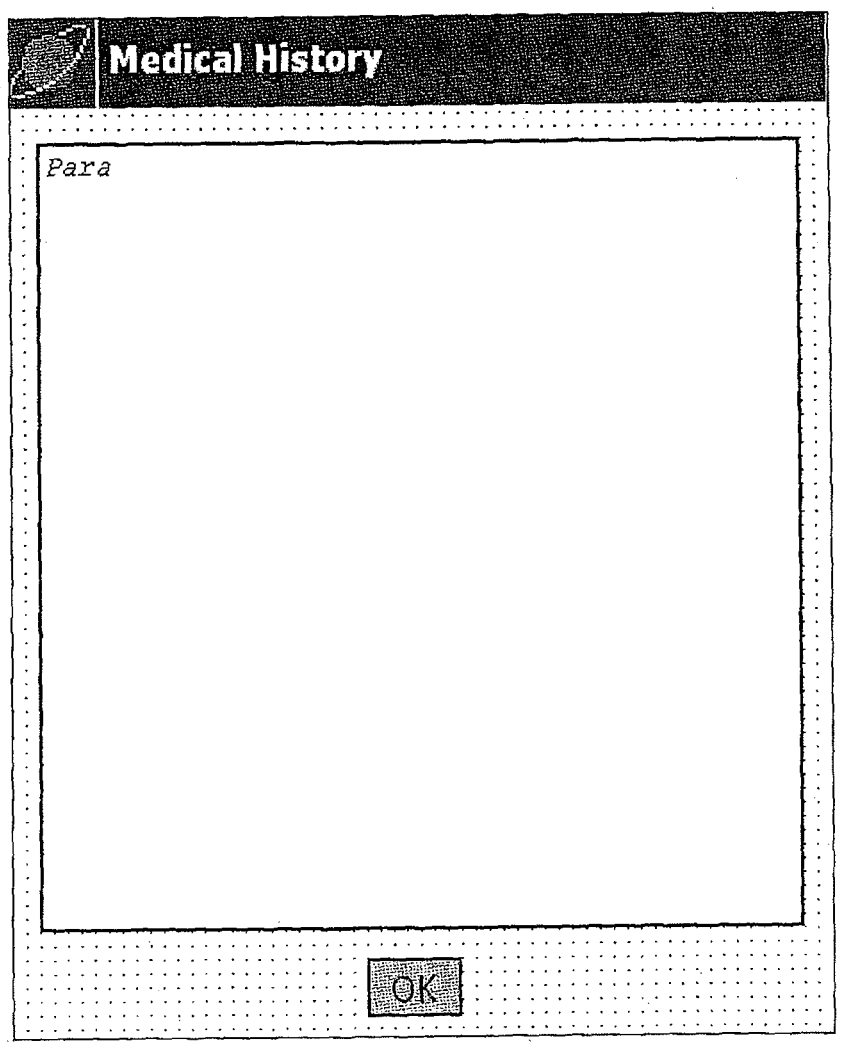

FIG. 72 shows an example of a user interface screen for allowing a caregiver to record textual information relating to a patient's medical history.

Figure 73:
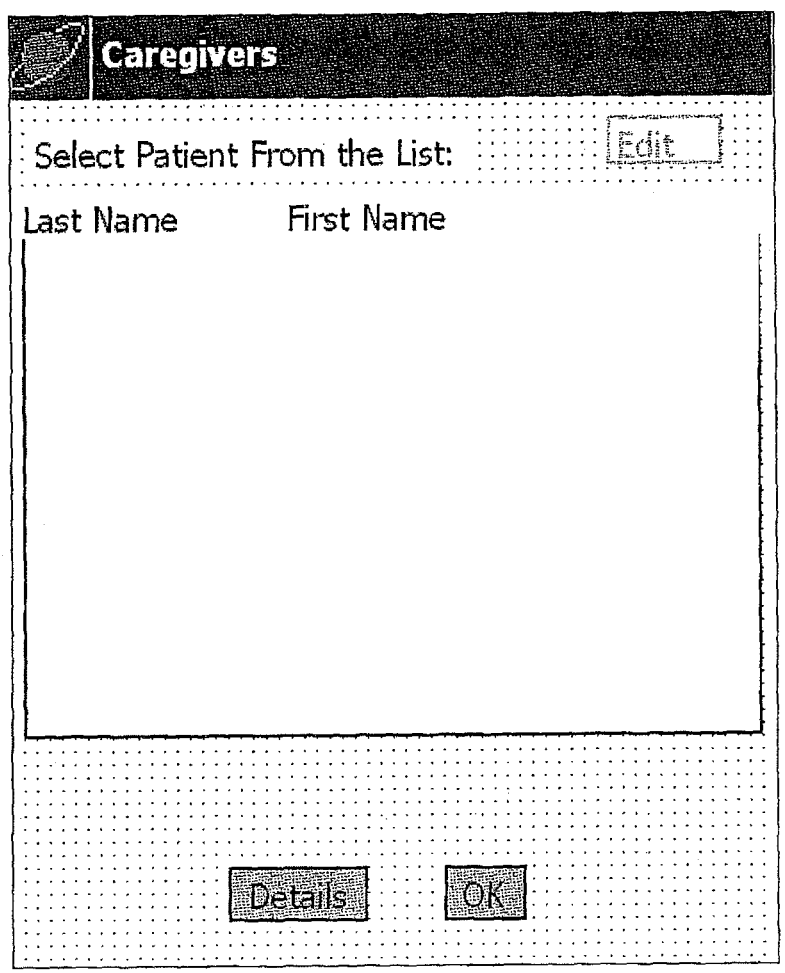

FIG. 73 shows an example of a user interface screen for allowing caregivers to be associated with patients.

FIG. 74 shows an example of a user interface screen for allowing detailed information about a caregiver, such as address and telephone information, to be recorded.

Figure 75:
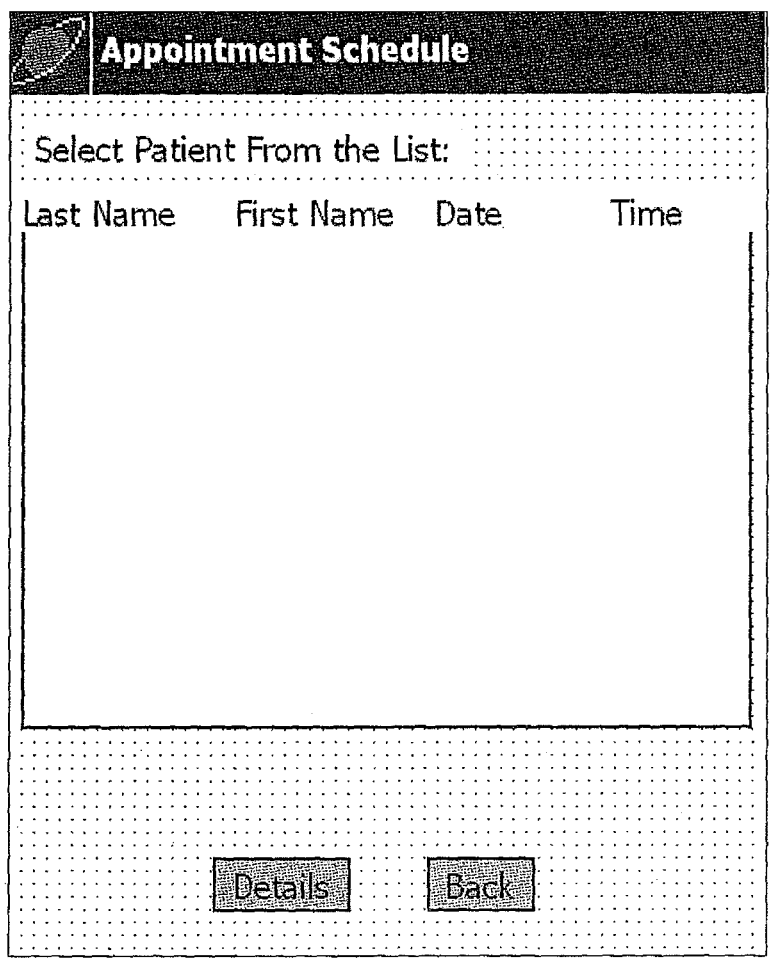

FIG. 75 shows an example of a user interface screen for allowing a caregiver to schedule appointments for visiting patients. Using this screen, the caregiver can select a patient from a list of patients under the caregiver's care, and can schedule one or more appointments for the patient. This can be accomplished by displaying a calendar screen to the caregiver (e.g., a calendar screen generated by the smart phone's operating system, or other calendar), whereupon appointments can be entered into the calendar.

FIG. 76 shows an example of a user interface screen for allowing a caregiver to provide detailed information regarding a scheduled visit for a patient. In this screen, the caregiver can input the patient ID, last name, first name, date and time of visit, and a description of the visit.

Figure 77:
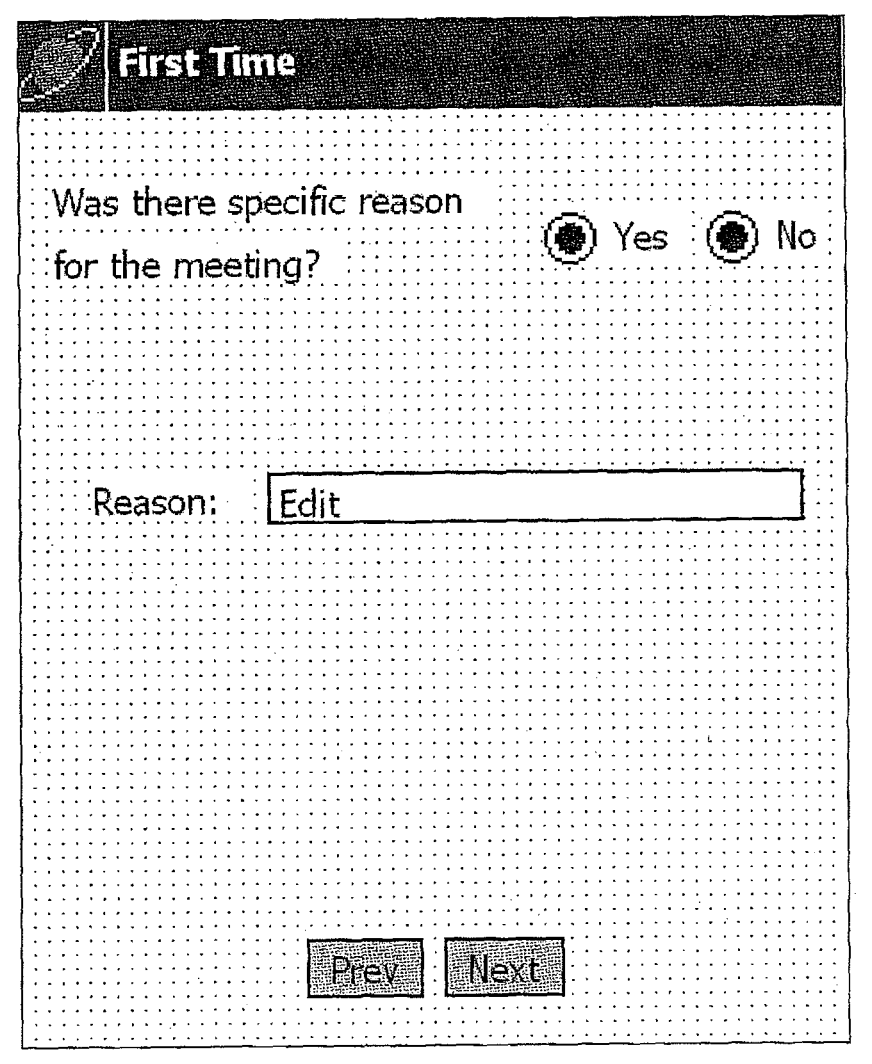

FIG. 77 shows an example of a user interface screen for allowing a caregiver to provide further information about a scheduled visit to a patient, such as whether there is a specific reason for the meeting, and if so, a description of the reason.

FIG. 78 shows an example of a user interface screen for allowing a caregiver to provide further information about patient cases, such as whether cases were committed, and if so, how many cases were committed and an indication of an expected time of receipt of demographics relating to the cases. If no cases have been committed, a reason can be provided in the screen.

FIG. 79 shows an example of a user interface screen for allowing a caregiver to input information relating to patient follow-ups. In this screen, the caregiver can identify whether a follow-up yielded additional cases, whether additional follow-ups are required, and if so, times and requirements for such follow-ups.

FIG. 80 shows an example of a user interface screen for allowing a caregiver to input additional information relating to patient follow-ups, such as the quantities and times of receipt by the caregiver of such cases.

FIG. 81 shows an example of a user interface screen for allowing a caregiver to input information relating to cases referred by a caregiver to a medical practitioner. In this screen, the caregiver can identify whether the practitioner's practice is currently receiving referred cases, the point of a visit to the practitioner by a patient, the identity of a person at the practitioner's office with whom the caregiver has spoken, and the result of a patient's visit with the practitioner.

FIG. 82 shows an example of a user interface screen for allowing a caregiver to identify specific personnel issues that the caregiver may be experiencing, such as whether the issue is related to a procedure that the caregiver has been asked to perform, a field nurse practitioner, or some other issue, as well as whether the issue has been resolved and whether any additional steps should be taken.

Importantly, the information captured by the system and method for remote monitoring and assessment of patients can be used in various ways by medical and other personnel. Doctors can use the system to remotely monitor the medical condition of a patient, and can remotely ascertain whether in-home treatment of the patient, as well as drugs prescribed by the doctor and/or medical equipment being used by the patient, are effective in stabilizing or improving the patient's condition. Further, supervisors of in-home caregivers can check on the care being provided the caregivers, and attention can quickly be given to issues that may arise while a patient is being treated by the caregiver. The system thus provides assistance with human resource management, by allowing for remote oversight, supervision, and management of medical personnel.

Also, for example, a pharmaceutical company could use data obtained through the system to conduct research into, for example, how often its drugs are prescribed by doctors and delivered to patients. This would allow the pharmaceutical company to focus marketing efforts on doctors and other medical personnel who are in the best position to prescribe certain drugs.

Having thus described the invention in detail, it is to be understood that the foregoing description is not intended to limit the spirit or scope thereof. What is desired to be protected is set forth in the following claims.

What is claimed is:

1. A system for remote patient monitoring and assessment to facilitate patient treatment, comprising:
   at least one portable computing device operated by a caregiver, the at least one portable computing device generating a plurality of user interface screens for allowing the caregiver to enter information relating to a patients medical condition and to treatment of the patient;
   a local assessment engine stored on and executed by the at least one portable computing device, the local assessment engine comparing a parameter of the information entered by the caregiver to a pre-defined threshold to determine whether the parameter is acceptable;
   wherein the at least one portable computing device is adapted to generate and display an alert screen on the at least one portable computing device if the local assessment engine determines that the parameter is unacceptable;
   wherein the at least one portable computing device is adapted to lock the user interface of the at least one portable computing device and display a screen to the caregiver requiring the caregiver to communicate with a supervisor if the local assessment engine determines that the parameter is unacceptable;
   a central server in communication with the portable computing device via a network, the central server receiving the information entered by the caregiver and electronically generating a report summarizing the patients medical condition and treatment given to the patient by the caregiver;
a transmitter adapted to transmit the report to a recipient;
a Global Positioning System (GPS) receiver for determining a location of the caregiver, the portable computing device adapted to transmit the location to the central server for processing by the central server and inclusion in the report;
wherein the at least one portable computing device is adapted to determine time spent by the caregiver at the patient's location, the portable computing device adapted to transmit the time to the central server for processing by the central server and inclusion in the report;
wherein the at least one portable computing device is adapted to schedule future appointments to visit the patient; and
wherein the at least one portable computing device is adapted to create a progress note relating to progress of a patient's treatment, and to transmit the progress note to a medical professional; and
wherein the plurality of user interface screens comprises a screen requiring the caregiver to enter the caregiver's signature.

2. The system of claim 1, wherein the alert screen displays a corrective action to be taken by the caregiver.

3. The system of claim 1, wherein the portable computing device comprises a camera for allowing the caregiver to take a photograph of the patient.

4. The system of claim 1, wherein the portable computing device comprises means for obtaining telemetry information from a medical device used by the patient.

5. The system of claim 4, wherein the portable computing device transmits the telemetry information to the central server, and the central server processes and includes the telemetry information in the report.

6. A method for remotely monitoring and assessing a patient to facilitate patient treatment, comprising the steps of:
providing a portable computing device to a caregiver;
displaying a plurality of user interface screens on the portable computing device;
allowing the caregiver to enter information relating to a patient's medical condition and treatment of the patient using the plurality of user interface screens on the portable computing device;
transmitting the information entered by the caregiver to a central server in communication with the portable computing device, the central server electronically generating a report summarizing the patient's medical condition and treatment given to the patient by the caregiver;
comparing a parameter of the information entered by the caregiver to a pre-defined threshold to determine whether the parameter is acceptable using a local assessment engine executing on the portable computing device;
displaying an alert screen on the portable computing device if the parameter 1s unacceptable;
locking the user interface of the portable computing device and displaying a screen to the caregiver requiring the caregiver to communicate with a supervisor if the parameter is unacceptable;
displaying on the portable computing device a screen which requires the caregiver to enter the caregiver's signature;
determining a location of the caregiver using the portable computing device;
transmitting the location to the central server for processing by the central server and inclusion in the report;
determining time spent by the caregiver at the patient's location;
transmitting the time to the central server for processing by the central server and inclusion in the report;
allowing the caregiver to schedule future appointments to visit the patient using the portable computing device; and
allowing the caregiver to create a progress note relating to progress of a patient's treatment and to transmit the progress note to a medical professional.

7. The method of claim 6, wherein the step of displaying the alert screen comprises displaying an alert screen including a corrective action to be taken by the caregiver if the parameter is unacceptable.

8. The method of claim 6, further comprising allowing the caregiver to take a photograph of the patient using a camera in the portable computing device.

9. The method of claim 6, further comprising obtaining, using the portable computing device, telemetry information from a medical device used by the patient.

10. The method of claim 9, further comprising transmitting the telemetry information to the central server, the central server processing and including the telemetry information in the report.

11. A non-transitory, computer-readable storage medium having computer-readable instructions for remotely monitoring and assessing a patient to facilitate patient treatment, wherein when the computer-readable instructions are executed by a portable computing device operated by a caregiver, cause the portable computing device to execute the steps comprising:
displaying a plurality of user interface screens on the portable computing device;
allowing the caregiver to enter information relating to a patient's medical condition and treatment of the patient using the plurality of user interface screens on the portable computing device;
transmitting the information entered by the caregiver to a central server in communication with the portable computing device, for subsequent electronic generation of a report summarizing the patient's medical condition and treatment given to the patient by the caregiver;
comparing a parameter of the information entered by the caregiver to a pre-defined threshold to determine whether the parameter is acceptable using a local assessment engine executing on the portable computing device;
displaying an alert screen on the portable computing device if the parameter is unacceptable;
locking the user interface of the portable computing device and displaying a screen to the caregiver requiring the caregiver to communicate with a supervisor if the parameter is unacceptable;
displaying on the portable computing device a screen which requires the caregiver to enter the caregiver's signature;
determining a location of the caregiver using the portable computing device;
transmitting the location to the central server for processing by the central server and inclusion in the report;
determining time spent by the caregiver at the patient's location;
transmitting the time to the central server for processing by the central server and inclusion in the report; and allowing the caregiver to schedule future appointments to visit the patient using the portable computing device.

12. The computer-readable medium of claim 11, wherein the step of displaying the alert screen comprises displaying an alert screen including a corrective action to be taken by the caregiver if the parameter is unacceptable.

13. The computer-readable storage medium of claim 11, further comprising allowing the caregiver to take a photograph of the patient using a camera in the portable computing device.

14. The computer-readable storage medium of claim 11, further comprising obtaining, using the portable computing device, telemetry information from a medical device used by the patient.

15. The computer-readable storage medium of claim 14, further comprising transmitting the telemetry information to the central server, the central server processing and including the telemetry information in the report.

16. A method for remotely monitoring and assessing a patient having an implanted infusion pump to facilitate patient treatment, comprising the steps of:
  providing a portable computing device to a caregiver;
    displaying a plurality of user interface screens on the portable computing device; allowing the caregiver to enter information relating to the implanted infusion pump using the plurality of user interface screens on the portable computing device;
    comparing a parameter of the information entered by the caregiver to a pre-defined threshold to determine whether the parameter is acceptable using a local assessment engine stored and executing on the portable computing device;
  displaying an alert screen on the portable computing device if the parameter is unacceptable;
  locking the user interface of the portable computing device and requiring the caregiver to communicate with a supervisor if the parameter is unacceptable; and allowing the caregiver to refill the implanted infusion pump if the parameter is acceptable;
allowing the caregiver to input medical information about the patient using the plurality of user interface screens; and
transmitting the medical information to a patient assessment server and generating a report at the server summarizing treatment of the patient by the caregiver.

17. A method for remotely monitoring and assessing a patient having an implanted infusion pump to facilitate patient treatment, comprising the steps of:
  providing a portable computing device to a caregiver;
  allowing the caregiver to withdraw fluid remaining in the implanted infusion pump;
  displaying a plurality of user interface screens on the portable computing device; allowing the caregiver to enter information relating to the fluid withdrawn from the implanted infusion pump using the plurality of user interface screens on the portable computing device;
  analyzing the information entered by the caregiver;
  comparing the information to an expected amount of remaining fluid using a local assessment engine stored and executing on the portable computing device;
  displaying an alert screen on the portable computing device if the information entered by the caregiver does not match the expected amount of remaining fluid; and locking the user interface of the portable computing device and requiring the caregiver to communicate with a supervisor if the information entered by the caregiver is unacceptable;
  calculating a range of acceptable remaining amounts using the portable computing device;
  comparing the information provided by the caregiver to the range of acceptable amounts; and
  displaying an alert screen if the information provided by the caregiver is outside of the range of acceptable amount.

* * * * *